United States Patent
Nagasawa et al.

(10) Patent No.: US 7,300,784 B2
(45) Date of Patent: Nov. 27, 2007

(54) NITRILE HYDRATASE AND A METHOD FOR PRODUCING AMIDES

(75) Inventors: Toru Nagasawa, Gifu (JP); Akinobu Matsuyama, Tsukuba (JP)

(73) Assignee: Daicel Chemical Industries, Ltd. (JP)

( * ) Notice: Subject to any disclaimer, the term of this patent is extended or adjusted under 35 U.S.C. 154(b) by 379 days.

(21) Appl. No.: 10/469,427

(22) PCT Filed: Mar. 1, 2002

(86) PCT No.: PCT/JP02/01912

§ 371 (c)(1), (2), (4) Date: Mar. 25, 2004

(87) PCT Pub. No.: WO02/070717

PCT Pub. Date: Sep. 12, 2002

(65) Prior Publication Data

US 2004/0209345 A1    Oct. 21, 2004

(30) Foreign Application Priority Data

Mar. 2, 2001 (JP) ............... 2001-059023
Jan. 24, 2002 (JP) ............... 2002-016222

(51) Int. Cl.
C12N 9/00 (2006.01)
C12N 9/88 (2006.01)
C12N 1/20 (2006.01)
C12N 15/00 (2006.01)
C07H 21/04 (2006.01)

(52) U.S. Cl. .................. 435/232; 435/183; 435/252.3; 435/320.1; 536/23.2

(58) Field of Classification Search ................ 435/183, 435/232, 252.3, 320.1; 536/23.2
See application file for complete search history.

(56) References Cited

U.S. PATENT DOCUMENTS

| 4,248,968 A | 2/1981 | Watanabe et al. |
| 5,130,235 A | 7/1992 | Beppu et al. |
| 5,648,256 A | 7/1997 | Yamada et al. |
| 5,731,176 A | 3/1998 | Yamada et al. |
| 5,753,472 A | 5/1998 | Yamada et al. |
| 5,789,211 A | 8/1998 | Yamada et al. |
| 6,043,061 A | 3/2000 | Ishii et al. |
| 2003/0124691 A1 | 7/2003 | Nagasawa et al. |

FOREIGN PATENT DOCUMENTS

| CN | 1218834 | 6/1999 |
| CN | 1054639 | 7/2000 |
| EP | 445646 | * 9/1991 |
| EP | 445646 A2 | 9/1991 |
| EP | 445646 A3 | 9/1991 |
| EP | 1055724 A1 | 11/2000 |
| JP | 63-137688 | 6/1988 |
| JP | 5-308980 | 11/1993 |
| JP | 2000-342292 | 12/2000 |

OTHER PUBLICATIONS

Teruhiko et al. Accession AAR13901, Nov. 25, 1991.*
Teruhiko et al. Accession AAR13902, Nov. 25, 1991.*
Kobayashi et al. "Cloning, nucleotide sequence and expression in *Escherichia coli* of two cobalt-containing nitrile hydratase genes from Rhodococcus rhodochrous J1." *Biochim. Biophys. Acta.* Dec. 2, 1991;1129(1):23-33.

* cited by examiner

*Primary Examiner*—Tekchand Saidha
*Assistant Examiner*—Christian L. Fronda
(74) *Attorney, Agent, or Firm*—Elizabeth A. Hanley, Esq.; Lahive & Cockfield, LLP

(57) ABSTRACT

An objective of the present invention is to provide a nitrile hydratase capable of producing 2-hydroxy-4-methylthiobutyroamide. The present invention provides a novel nitrile hydratase producing α-hydroxyamide using, α-hydroxnitrile as the substrate, and the encoding DNA thereof. The enzyme can be obtained from *Rhodococcus* sp. Further, the enzymatic activity of the enzyme can he maintained stably during the reaction. The present invention provides a method for producing amide compounds, the method comprising the step of reacting this enzyme to nitrile compounds. According to the present invention, from hydroxy nitrile compounds, corresponding amide compounds can be produced biochemically without reducing the enzyme activity of nitrile hydratase.

7 Claims, 14 Drawing Sheets

(Lineweaver-Burk plots)

(S-V plots)

(Lineweaver-Burk plots)

Figure 12

```
ctgcagtgtgcgcggcccgggacgagcgacggggtctcgaggactcgtccaccatgctcgccgatccggg
gggcagacgaaaagacaatgagttgagtgaatgaggcgtaactgaatctagactagtgggggcctgtcgg
gttgtccagagcgtgtcgtcgcgcgcaggaaagcgtcaaaaatcaactgccgcaacgtttgctccggaat
gaggcagctcccctgttgcgcccatgcgggggagtctgccctctggatcccccgtgcgagaggcaacaaa
atcttaacaggtcacgaagtcatgacctattgacctatcgggattgtggtgtttaaggttggtgacccaa
gccacaaggaggcaatgcg
```

*ATGGATGGTATCCACGATCTGGGCGGGCGCGCCGGTCTGGGGCCGGTCAATCC*
*CGAACCCGGTGAGCCGGTCTTTCATTCTCGTTGGGAGCGGTCGGTTTTGACGATGTTTCCGGCCATGGCGTTA*
*GCCGGGGCGTTCAACCTCGACCAGTTCCGGGGCGCGATGGAACAGATTCCCCCGCACGACTATCTGACCTCGC*
*AGTACTACGAGCACTGGATGCACGCGATGATCCACTACGGCATCGAGGCGGGCATCTTCGACCCGAACGAGCT*
*CGACCGTCGCACCCAGTACTACCTGGAGCATCCGGACGAAGACCCGCCCCTGCGGCAGGACCCGCAGTTGGTG*
*GAGACGATCTCGCAGTTGATCATGCACGGAGCCGACTACCGAAGGCCGACCGACGCCGAGGGCGTCTTCGCGG*
*TGGGCGACAAGGTCGTTGTGCGGTCGGACGCCTCGCCGAACACCCACACCCGTCGCGCCGGCTACATCCGTGG*
*ACGCACCGGTGAGATCGTCGCAGCTCACGGCGCCTACGTTTTCCCGGACACTAACGCCGTCGGCGCCGGCGAA*
*CACCCCGAACACCTGTACACGGTGCGGTTCTCGGCGACCGAGTTGTGGGGCGAGACCGCCACCTCCAACGCGG*
*TCAACCACATCGACGTGTTCGAACCCTACCTGCTGCCGGCCTGA* β

```
                                      ccggagcgtccgatacaacctcgctga
taccccactgccccgcctacggaaacgagttcacccg
```

*ATGACCGCCCACAATCCCGTCCAGGGCACCTTCC*
*CCCGATCGAACGAGGAGATCGCCGCCCGCGTCAAGGCCATGGAGGCCATCCTCGTCGACAAGGGCCTGATCTC*
*CACCGACGCCATCGACTACATGTCCTCGGTCTACGAGAACGAGGTCGGTCCTCAGCTCGGCGCCAAGATCGCC*
*GCCCATGCCTGGGTCGATCCCGAGTTCAAACAGCGCCTGCTCGCCGACGCAACCGGCGCCTGCAAGGAAATGG*
*GCGTCGGCGGGATGCAGGGCGAAGAAATGGTCGTGCTGGAAAACACCGACACCGTCAACAACATGGTCGTGTG*
*CACCCTGTGCTCGTGCTACCCGTGGCCGGTGCTCGGATTGCCGCCCAACTGGTACAAGTACCCCGCCTACCGC*
*GCCCGCGCCGCCCGCGACCCGCGAGGGGTGATGGCCGAGTTCGGCTATACCCCCGCCTCGGACGTCGAGATCC*
*GGGTGTGGGACTCGAGCGCCGAACTGCGCTACTGGGTGCTGCCGCAGCGCCCCGCCGGCACCGAGAACTTCAC*
*CGAAGAGCAGCTCGCCGCCCTCGTCACCCGCGACTCGCTCATCGGCGTGTCCGTCCCCACCGCACCGAACAAG*
*GCCTGA* α

```
        catgccccaactcaacgaacaacccagccaggacctcaaggaccgcctcgacggcctggtgcaga
acctaccgttcaacgagcagattccccggcgctccggggaggtcgccttcgaccatgcctgggagatccg
cgctttcagcatcgccaccgccctgcatgcccagggccggttcgagtgggacgaattccagtcccgcctg
atcgactcgatcaaacagtgggaaaccgaacacaccaccaccgaggagtggagctactacgagtgttgga
tgctcgcactcgaagagctggtgcgggacaagggggctggtcgccggtgatgaactcgagcaccgcaccga
gcaggtgctggccaccccggccaacgccaccaccaacacgctgtacgcgacccccattgccgtgcacacc
agcgaagtacctactgctcagtactcccggtagcccctggggcctcgccttcacggaggtggaactctcg
tgtaaaggctcctgggctctgcgacgtagagataccaccgatctttctcttgggctccccaggagccgaa
gacgcatccctgatatggcaactcggacctggccgggcgcgcagacacaacgtgcgagcgccccggaact
tccaagcctctggcgtattcggaagacgctgcgaattagtcgaaggacaagggtttgaccagtaccgcaa
tgacaccgcaccgcatgggcggtgcgtggactcgtacagagcgccagcggctggcatcggttgtcggcgc
cgtcgtgatcctgcatgtattgggcgtggccctgtatgtgggatactccggtaatccagcagccgccgga
ggcctcgccggatccggtgtgctcgcctacgtgctcggcgtccgccacgcattcgacgccgatcacctcg
ctgccatcgatgacaccacgcgcctgatgctgttgcgcggacgccgtccggtcggggtcgggttcttctt
cgcgatgggacactcgaccgtcgtcattgtccttgctctggtcgtggcgctgggcgccagctccctgacc
acgagtgagctcgaggggggtccaggagatcggcggaatggtcgcgacggtcgtcgccgtagccttcttgc
tggtcgtcgccggactcaacagcgtggtcctgcgcaatctgctctccctggcccgacgggtgcggaccgg
ggcggacatcgcaggtgatctcgagagcagcctcagcgagcgtgggttgttcgcccggctgctcggtgcc
cgctggcgtggactgattcgttcgtcctggcacatgtatccggtcgggctgttgatggggctcgggctcg
agaccgcatccgaggtcaccctgctcactctcactgcttcggcggtgaccgggggcaccttgtccgtggc
tgcagcgggctcacggacggatcggccgccagatagtcgctcgcggtgcgcgccagatgccagttctgca
g
```

Figure 13

```
CrNH-α    1:MTAHNPVQGTFPRSNEEIAARVKAMEAILVDKGLISTDAIDYMSSVYENEVGPQLGAKIA
J1 L-α    1:MTAHNPVQGTLPRSNEEIAARVKAMEAILVDKGLISTDAIDHMSSVYENEVGPQLGAKIV
            ********** ***************************** ******************
CrNH-α   61:AHAWVDPEFKQRLLADATGACKEMGVGGMQGEEMVVLENTDTVNNMVVCTLCSCYPWPVL
J1 L-α   61:ARAWVDPEFKQRLLTDATSACREMGVGGMQGEEMVVLENTGTVHNMVVCTLCSCYPWPVL
          * ************* *** ** ****************** ** ***************
CrNH-α  121:GLPPNWYKYPAYRARAARDPRGVMAEFGYTPASDVEIRVWDSSAELRYWVLPQRPAGTEN
J1 L-α  121:GLPPNWYKYPAYRARAVRDPRGVLAEFGYTPDPDVEIRIWDSSAELRYWVLPQRPAGTEN
          **************** ****** ******* ***** ** *******************
CrNH-α  181:FTEEQLAALVTRDSLIGVSVPTAPNKA
J1 L-α  181:FTEEQLADLVTRDSLIGVSVPTTPSKA
          ******* ************** * **
```

Figure 14

```
CrNH-β    1:MDGIHDLGGRAGLGPVNPEPGEPVFHSRWERSVLTMFPAMALAGAFNLDQFRGAMEQIPP
J1 L-β    1:MDGIHDLGGRAGLGPIKPESDEPVFHSDWERSVLTMFPAMALAGAFNLDQFRGAMEQIPP
            **************  ** ****** ************************************

CrNH-β   61:HDYLTSQYYEHWMHAMIHYGIEAGIFDPNELDRRTQYYLEHPDEDPPLRQDPQLVETISQ
J1 L-β   61:HDYLTSQYYEHWMHAMIHHGIEAGIFDSDELDRRTQYYMDHPDDTTPTRQDPQLVETISQ
            ****************** ******** ********* *** *   * ************

CrNH-β  121:LIMHGADYRRPTDAEGVFAVGDKVVVRSDASPNTHTRRAGYIRGRTGEIVAAHGAYVFPD
J1 L-β  121:LITHGADYRRPTDTEAAFAVGDKVIVRSDASPNTHTRRAGYVRGRVGEVVATHGAYVFPD
            ** ********** *  ******* **************** *** ** ** *******

CrNH-β  181:TNAVGAGEHPEHLYTVRFSATELWGETATSNAVNHIDVFEPYLLPA
J1 L-β  181:TNALGAGESPEHLYTVRFSATELWGEPAAPNVVNHIDVFEPYLLPA
            *** **** *****************  *  * * **********
```

NITRILE HYDRATASE AND A METHOD FOR PRODUCING AMIDES

TECHNICAL FIELD

The present invention relates to a novel nitrile hydratase and a method for producing amide compounds from nitrile compounds using the nitrile hydratase.

BACKGROUND ART

To improve the expression level of nitrile hydratase, methods that overexpress nitrile hydratase in microorganism cells by genetic engineering and that convert nitrile compounds to the corresponding amide compounds using the cells have been examined. For example, known nitrile hydratases are derived form the following microorganisms. All of the nitrile hydratases are enzymes consisting of two types of heterogeneous subunits.

The genus *Rhodococcus* (Examined Published Japanese Patent Application (JP-B) NO. Hei 3-54558)

The genus *Rhodococcus* (Unexamined Published Japanese Patent Application (JP-A) NO. Hei 2-119778)

The genus *Pseudomonas* (JP-A Hei 3-251184) The genus *Rhodococcus rhodochrous* (EP Patent Application NO. 455646)

However, in all cases, the expression level of nitrile hydratase activity is not high enough with *E. coli* transformed with an expression plasmid containing an insert fragment of any nitrile hydratase gene described in these patent publications; the nitrile-hydrating activity per weight of cells of the transformant is lower than that of the original microorganism from which the gene is derived (Ikehata, O., Nishiyama, M., Horinouchi, S. and Beppu, T. "Primary structure of nitrile hydratase deduced from the nucleotide sequence of a *Rhodococcus* speices N-774 and its expression in *Escherichia coli*" Eur. J. Biochem. 181(1989), 563-570; Nishiyama, M., Horinouchi, S., Kobayashi, M., Nagasawa, T., Yamada, H. and Beppu, T. "Cloning and Characterization of Genes Responsible for Metabolism of Nitrile Compounds from Pseudomonas chlororaphis B23" Journal of bacteriology 173 (1991):2465-2472; Kobayashi, M., Nishiyama, M., Nagasawa, T., Horinouchi, S., Beppu, T. and Yamada, H. "Cloning nucleotide sequence and expression in *Escherichia coli* of two cobalt-containing nitrile hydratase genes from *Rhodococcus rhodochrous* J1" Biochimica et Biophysica Acta. 1129 (1991):23-33).

As mentioned above, it has been possible to express the nitrile hydratase activity itself in *E. coli* by genetic recombination techniques. However, so far, there is no available transformant having so high nitrile hydration activity as to be used for the industrial production of amides.

On the other hand, a nitrile hydratase, which exhibits very high nitrile hydration activity, has been found in *Achromobacter xerosis* (IFO 12668), and the gene encoding the enzyme has been cloned. Further, the gene was introduced into *E. coli* using an expression plasmid, and nitrile hydratase was overproduced with the resulting transformant (JP-A Hei 8-266277). This report shows only examples of acrylamide and α-hydroxyisobutylamide production, and thus there is no description on the activity of this enzyme toward 2-hydroxy-4-methylthiobutyronitrile in the report.

Thus, little is known about nitrile hydratases that can use 2-hydroxy-4-methylthiobutyronitrile (hereinafter abbreviated as HMBN) as a substrate. Furthermore, there is no previous method for producing 2-hydroxy-4-methylthiobutylamides (hereinafter abbreviated as HMBAm) from 2-hydroxy-4-methylthiobutyronitrile using *E. coli* transformed with an expression plasmid containing the nitrile hydratase gene as an insert fragment.

On the other hand, with respect to the production of α-hydroxyamide by microorganism, there is a known method for producing the corresponding amides from lactonitrile, hydroxyacetonitrile, α-hydroxy methylthiobutyronitrile and such, using microorganisms belonging to the genus *Bacilidium*, the genus *Bacteridium*, the genus *Micrococcus* or the genus *Brevibacterium* (see JP-B Sho 62-21519). In addition, there also exists a publicly known method for producing mandelamide from cyanohydrin (see JP-A Hei 4-222591; JP-A Hei 8-89267).

However, the enzymes having the nitrile hydratase activity capable of converting nitrile compounds to amide compounds have a problem that the enzymes readily lose their own enzymatic activities due to the presence of the nitrile compound as starting material or amide compound as the product. If the concentration of nitrile compound is raised in order to increase the rate of amidation, the nitrile hydratase is readily inactivated in a short period of time, and thus it is hard to obtain amide compound as the reaction product in a desired period of time. In addition, the amide compounds as the products also readily inactivate the nitrile hydratase, and thus it is difficult to obtain a high concentration of amide compound.

Furthermore, in varying degree depending on the type of compound, α-hydroxynitrile has been known to be partially decomposed to the corresponding aldehyde and hydrocyanic acid in a polar solvent (see V. Okano et al., J. Am. Chem. Soc., Vol. 98, 4201 (1976)). In general, aldehydes are linked to proteins and can inactivate the enzymatic activity (see Chemical Modification of Proteins, G. E. Means et al., Holden-Day, 125(1971)). Further, like aldehyde, hydrocyanic acid (cyanide) can also inhibitorily act on many enzymes. Thus, aldehyde and cyanide produced from α-hydroxynitrile as the starting material can be the cause of decreased enzymatic activity. Because of a problem that the enzyme is inactivated in a short period of time in the enzymatic hydration or hydrolysis of α-hydroxy nitrile, it was difficult to obtain a high concentration of α-hydroxyamide with high productivity.

To prevent the loss of enzymatic activity, various methods for increasing the enzymatic activity or for suppressing the loss of enzymatic activity (inactivation) have been tested. Such attempts include, for example, the following:

The reaction is carried out at a lower temperature ranging from the freezing point to 15° C. (JP-B Sho 56-38118).

A lower concentration of substrate is continuously supplied from multiple supply ports (JP-B Sho 57-1234).

A microorganism or processed product thereof is treated with an organic solvent (JP-A Hei 5-308980).

The reaction is carried out in the presence of higher unsaturated fatty acid (JP-A Hei 7-265090).

The microorganism cells are subjected to crosslinking treatment with glutaraldehyde and such (JP-A Hei 7-265091; JP-A Hei 8-154691).

The concentration of hydrocyanic acid contaminated in the nitrile compound is lowered by a chemical method, and then nitrile hydratase is allowed to react with the nitrile compound (see JP-A Hei 11-123098).

The long-term stabilization of the enzymatic activity is achieved by the presence of sulfite ion, acid sulfite ion or dithionite ion (see JP-A Hei 8-89267)

Aldehyde is added (see JP-A Hei 4-222591).

None of these methods had sufficient effects on the industrial applications. Although some of the methods were effective, they had room for economical or practical improvement. For example, the above-mentioned method adding aldehyde requires a large quantity of aldehyde in 1-5 times molar excess of cyanohydrin as the start material, and thus the method was less than an economical solution. Similarly, it is illustrated that the method adding sulfite ion, acid sulfite ion or dithionite ion requires addition of the ion in an amount equivalent to or larger than that of the starting material, and thus the method was not practical one.

An objective of the present invention is to provide a nitrile hydratase having high nitrile-hydrating activity. Another objective of the present invention is to provide a stable nitrile hydratase capable of maintaining the high enzymatic activity over a long period of time. In addition, still another important objective of the present invention is to provide a nitrile hydratase capable of also using 2-hydroxy-4-methylthiobutyronitrile as a substrate.

Furthermore, another objective of the present invention is to provide the gene encoding nitrile hydratase having high nitrile hydration activity, recombinant plasmid containing the gene and transformant containing the recombinant plasmid. In addition, yet another objective of the present invention is to provide a method for producing the corresponding amides from nitrile using the transformant expressing high nitrile hydration activity.

DISCLOSURE OF THE INVENTION

The present inventors strenuously studied to achieve the above-mentioned objectives, and found nitrile hydratase having very high nitrile hydration activity in microorganisms belonging to the genus Rhodococcus (Rhodococcus sp.). Then, the present inventors confirmed that the nitrile hydratase was a novel enzyme usable for achieving the above-mentioned objectives, and thus completed the present invention.

The inventors then cloned the gene encoding the enzyme by recombinant DNA technology, and prepared E. coli transformed with the expression plasmid comprising an expression vector containing the isolated gene as an insert. Further, the present inventors succeeded in the large-scale production of the nitrile hydratase with the obtained transformant and thus completed the present invention.

Namely, the present invention provides the following nitrile hydratase, polynucleotide encoding the enzyme, method for producing the enzyme and method for producing amides using the enzyme of the present invention.

The nitrile hydratase of the present invention has the following physicochemical properties (a) and (b):
(a) acting on the nitrile group of nitrile compound, hydrating the nitrile group and converting it to an amide group; and,
(b) being cyanide-resistant.

In the present invention, the activity of hydrating the nitrile group of nitrile compound and converting it to an amide group is referred to as "nitrile hydratase activity". Preferably, an enzyme capable of acting on the compound of the following formula (1) and producing the amide compound of formula (3) is designated as "nitrile hydratase".

Formula (1):

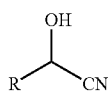

(1)

Formula (3):

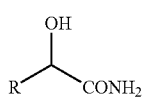

(3)

(Where R represents substituted or unsubstituted alkyl group, substituted or unsubstituted alkenyl group, substituted or unsubstituted cycloalkyl group, substituted or unsubstituted alkoxy group, substituted or unsubstituted aryloxy group, substituted or unsubstituted saturated or unsaturated heterocyclic group).

Preferably, the nitrile hydratase of the present invention can act on 2-hydroxy-4-methylthiobutyronitrile and produce 2-hydroxy-4-methylthiobutyroamide.

The nitrile hydratase activity of the present invention can be confirmed as follows. At first, an enzyme sample is added to a 0.1 M potassium phosphate buffer (pH 6.5) containing 10% v/v 2-hydroxy-4-methylthiobutyronitrile (HMBN) as the substrate. Instead of the enzyme sample, microorganism cells and crude enzyme are also usable. After addition of enzyme, the solution is incubated at 20° C. for 15 minutes. The reaction solution is then combined with an excess volume of 0.1% (v/v) phosphate solution, and the mixture is shaken vigorously to stop the reaction. The reaction product can be analyzed by HPLC.

According to this assay method, 1 U of nitrile hydratase was defined as the amount of enzyme capable of producing 1 µmol nicotinamide at 20° C. for 1 minute in a reaction solution with a standard composition; 1 U was defined as the amount of enzyme capable of producing 1 µmol HMBAm at 20° C. for 1 minute in a reaction solution with a standard composition.

Specifically, for example, the enzymatic activity can be assayed by the procedure as described in Examples. Further, protein quantification is carried out by the dye-binding method using a protein assay kit from Bio-Rad.

On the other hand, as used herein, "cyanide resistance" means that the enzyme retains 40% or more nitrile hydratase activity when treated at 20° C. for 30 minutes in the presence of 1 mM cyanide ion. Alternatively, when the enzyme retains 10% or more nitrile hydratase activity after treated at 20° C. for 30 minutes in the presence of 5 mM cyanide ion, one can state that the enzyme is cyanide-resistant.

Further, the present invention provides nitrile hydratase having the following physicochemical properties (1)-(7):

(1) Molecular Weight:
The molecular weight is approximately 110,000 Da when determined by gel filtration;
The enzyme is separated to two subunits of 26.8 kDa and 29.5 kDa by SDS-polyacrylamide gel electrophoresis.

(2) Action:
The enzyme acts on the nitrile group of nitrile compound.

(3) Optimal pH:
The activity of hydrating nitrile group is maximized at pH 5.5-6.5.

(4) Optimal Temperature:
The activity of hydrating nitrile group is maximized at 40-45° C.

(5) pH Stability:
The enzyme is stable within pH 4-9.

(6) Thermal Stability:
The enzyme retains 70% or more activity after heat-treated at 50° C. for 30 minutes.

(7) Inhibitor:
The enzyme is inhibited by $HgCl_2$, $AgNO_3$, hydroxylamine or phenylhydrazine.

Further, the present invention provides nitrile hydratase having the following physicochemical properties (c) and/or (d) in addition to the above-mentioned physicochemical properties (a) and (b), or (1)-(7)

(c) Substrate Specificity:

The enzyme uses 2-hydroxy-4-methylthiobutyronitrile as the substrate and produces 2-hydroxy-4-methylthiobutyroamide.

(d) Stabilization:

The enzyme is stabilized by divalent metal ions.

In the present invention, the substrate specificity of nitrile hydratase can be determined by the method for testing the activity nitrile hydratase as described above. Further, as used herein, "stabilized by divalent metal ions" means that the enzymatic activity is not substantially reduced even when the enzyme is incubated with 1.8 w/w % 2-hydroxy-4-methylthbutyronitrile in the presence of a divalent metal ion for 20 minutes. In a preferred embodiment of the present invention, the nitrile hydratase of the present invention can maintain 110% or higher activity under these conditions.

In the present invention, the above-mentioned divalent metal ion includes nickel ion and cobalt ion. These divalent metal ions enhance the enzymatic activity of nitrile hydratase of the present invention at a concentration of 0.1 mM-1 M, generally 0.5-100 mM, preferably 1-10 mM.

The nitrile hydratase of the present invention can be purified from microorganisms capable of producing the enzyme by commonly used protein purification methods. The above microorganisms can be cultured in a standard bacterial culture medium. Some compounds for inducing the expression of nitrile hydratase can be added to the medium. For example, the addition of a nitrile compound or amide compound can enhance the activity of nitrile hydratase. More specifically, acetonitrile, acetamide and such can be used as the enzyme-inducer.

Microorganisms capable of producing the enzyme are sufficiently grown, and then the cells are harvested. The cells are lysed in an appropriate buffer to prepare cell-free extract. The buffer can contain a reducing agent such as 2-mercaptoethanol, protease inhibitor such as phenylmethanesulfonyl fluoride (PMFS). The nitrile hydratase can be purified from the cell-free extract by fractionation based on the protein solubility and appropriate combinations of various chromatographic procedures.

As a fractionation method based on the protein solubility, for example, precipitation with an organic solvent such as acetone and dimethylsulfoxide or salting out with ammonium sulfate can be used. On the other hand, known chromatographic methods include cation-exchange chromatography, anion-exchange chromatography, gel filtration, hydrophobic chromatography as well as many procedures of affinity chromatography using dye, antibody and others. More specifically, the nitrile hydratase of the present invention can be purified as an electrophoretically homogeneous polypeptide, for example, by hydrophobic chromatography using phenyl-TOYOPEARL, anion-exchange chromatography using DEAE-Sepharose, hydrophobic chromatography using butyl-TOYOPEARL, affinity chromatography using Blue-Sepharose, gel filtration using Superdex 200, and others.

Microorganisms that can be used for this purpose include, for example, those belonging to the genus *Rhodococcus* (*Rhodococcus* sp.) More specifically, *Rhodococcus* sp. Cr4 is a suitable microorganism for producing the nitrile hydratase of the present invention. *Rhodococcus* sp. Cr4 has been deposited under the accession number of FERM BP-6596 in the International Patent Organism Depositary.

International Deposition of *Rhodococcus* sp. Cr4:

(a) Name and Address of Depositary Institute

Name: International Patent Organism Depositary, National Institute of Advanced Industrial Science and Technology (AIST), Independent Administrative Institution (Previous Name: The National Institute of Bioscience and Human-Technology, The Agency of Industrial Science and Technology, The Ministry of International Trade and Industry)

Address: Chuo 6, 1-1, Higashi 1-chome, Tsukuba-shi, Ibaraki 305-8566 Japan (b) Date of Deposition (Original Date of Deposition): Dec. 8, 1998

(c) Accession Number: FERM BP-6596

The nitrile hydratase of the present invention is that can be obtained from *Rhodococcus* sp. Cr4 is a novel enzyme having the above-mentioned physicochemical properties (a)-(d) and (1)-(7). The structural feature is described above as the physicochemical property (1); the enzyme is a heterodimeric polypeptide consisting of α-subunit of 26.8 kDa and β-subunit of 29.5 kDa, determined by SDS-PAGE. The amino acid sequence of α-subunit is shown in SEQ ID NO: 2 (226 amino acid residues) and the amino acid sequence of β-subunit, in SEQ ID NO: 4 (207 amino acid residues). Namely, the present invention provides the following substantially pure protein complex having the nitrile hydratase activity.

The present invention relates to a substantially pure protein complex between polypeptide comprising the amino acid sequence of SEQ ID NO: 2 and polypeptide comprising the amino acid sequence of SEQ ID NO: 4. Further the present invention includes a homologue of the protein complex between polypeptide comprising the amino acid sequence of SEQ ID NO: 2 and polypeptide comprising the amino acid sequence of SEQ ID NO: 4.

The term "substantially pure" as used herein in reference to a given protein, polypeptide, or protein complex means that the protein, polypeptide, or protein complex is substantially free from other biological macromolecules. The substantially pure protein, polypeptide, or protein complex is at least 75% (e.g., at least 0.80, 85, 95, or 99%) pure by dry weight. Purity can be measured by any appropriate standard method known in the art, for example, by column chromatography, polyacrylamide gel electrophoresis, or HPLC analysis.

The protein complex of the present invention is a nitrile hydratase that can be expressed by genetic recombination techniques using isolated polynucleotides encoding the nitrile hydratase of the present invention. The polynucleotides encoding the nitrile hydratase of the present invention can be isolated, for example, by the following method.

The nitrile hydratase provided by the present invention consists of α-subunit encoded by the polynucleotide shown in any one of (A)-(E), and β-subunit encoded by the polynucleotide shown in any one of (a)-(e), and is a protein complex having the following physicochemical properties (i) and (ii).

(i) Effect:

Acting on the nitrile group of nitrile compound, hydrating the nitrile group and converting it to an amide group; and (ii) Substrate Specificity:

The enzyme uses 2-hydroxy-4-methylthiobutyronitrile as the substrate and produces 2-hydroxy-4-methylthiobutyroamide.

The polynucleotide shown in any one of the following (A)-(E) can be used as the gene encoding α-subunit constituting the protein complex of the present invention. In the present invention, the polynucleotide shown in any one of (A)-(E) is useful for expressing the α-subunit of nitrile hydratase of the present invention:

(A) a polynucleotide comprising the nucleotide sequence of SEQ ID NO: 1;

(B) a polynucleotide encoding polypeptide comprising the amino acid sequence of SEQ ID NO: 2;

(C), a polynucleotide encoding polypeptide comprising the amino acid sequence of SEQ ID NO: 2, which contains one or more amino acid substitutions, deletions, insertions and/or additions;

(D) a polynucleotide capable of hybridizing to a polynucleotide comprising the nucleotide sequence of SEQ ID NO:1 under stringent conditions;

(E) a polynucleotide encoding polypeptide having 70% or higher identity to the amino acid sequence of SEQ ID NO: 2.

Moreover, the polynucleotide shown in any one of the following (a)-(e) can be used as the gene encoding β-subunit constituting the protein complex of the present invention. In the present invention, the polynucleotide shown in any one of (a)-(e) is useful for expressing the α-subunit of nitrile hydratase of the present invention:

(a) a polynucleotide comprising the nucleotide sequence of SEQ ID NO: 3;

(b) a polynucleotide encoding polypeptide comprising the amino acid sequence of SEQ ID NO: 4;

(c) a polynucleotide encoding polypeptide comprising the amino acid sequence of SEQ ID NO: 4, which contains one or more amino acid substitutions, deletions, insertions and/or additions;

(d) a polynucleotide capable of hybridizing to a polynucleotide comprising the nucleotide sequence of SEQ ID NO: 3 under stringent conditions;

(e) a polynucleotide encoding polypeptide having 70% or higher identity to the amino acid sequence of SEQ ID NO: 4.

The present invention relates to isolated polynucleotides encoding subunits of the nitrile hydratase and homologues thereof.

As used herein, an "isolated polynucleotide" is a polynucleotide the structure of which is not identical to that of any naturally occurring polynucleotide or to that of any fragment of a naturally occurring genomic polynucleotide spanning more than three separate genes. The term therefore includes, for example, (a) a DNA which has the sequence of part of a naturally occurring genomic DNA molecule in the genome of the organism in which it naturally occurs; (b) a polynucleotide incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion polypeptide. Specifically excluded from this definition are polynucleotides of DNA molecules present in mixtures of different (i) DNA molecules, (ii) transfected cells, or (iii) cell clones; e.g., as these occur in a DNA library such as a cDNA or genomic DNA library.

Accordingly, in one aspect, the invention provides an isolated polynucleotide that encodes a polypeptide described herein or a fragment thereof. Preferably, the isolated polynucleotide includes a nucleotide sequence that is at least 60% identical to the nucleotide sequence shown in SEQ ID NO: 1 or 3. More preferably, the isolated nucleic acid molecule is at least 65%, 70%, 75%, 80%, 85%, 90%, 91%, 92%, 0.93%, 94%, 0.95%, 96%, 97%, 98%, 99%, or more, identical to the nucleotide sequence shown in SEQ ID NO: 1 or 3. In the case of an isolated polynucleotide which is longer than or equivalent in length to the reference sequence, e.g., SEQ ID NO: 1 or 3, the comparison is made with the full length of the reference sequence. Where the isolated polynucleotide is shorter than the reference sequence, e.g., shorter than SEQ ID NO: 1 or 3, the comparison is made to segment of the reference sequence of the same length (excluding any loop required by the homology calculation).

Each of the nucleotide sequences of polynucleotides encoding α-subunit and β-subunit of nitrile hydratase of the present invention as well as the amino acid sequences encoded by the nucleotide sequences are novel. Based on the information of the nucleotide sequences revealed in the present invention, the genes of interest can be obtained form the deposited microorganism as described above. The genes can be obtained by PCR or screening with hybridization technique. The full-length genes can also be obtained by chemical DNA synthesis.

Further, based on the information on the above nucleotide sequences, it is possible to obtain the nitrile hydratase gene derived from other organisms. For example, the nitrile hydratase genes derived from various organisms can be isolated by performing, under stringent conditions, hybridization to polynucleotides prepared from other organisms, using the above nucleotide sequence or a partial sequence thereof as a probe.

The term "polynucleotide capable of hybridizing under stringent conditions" means a polynucleotide capable of hybridizing to a polynucleotide, which has a nucleotide sequence selected from the nucleotide sequences of SEQ ID NO: 1 (α-subunit) and SEQ ID NO: 3 (β-subunit), as a probe, for example, with an ECL direct nucleic acid labeling and detection system (Amersham Pharmacia Biotech) under the conditions as described in the manual (wash: with a primary wash buffer containing 0.5×SSC at 42° C.). Also included in the invention is a polynucleotide that hybridizes under high stringency conditions to the nucleotide sequence of SEQ ID NO: 1 or a segment thereof as described herein. "High stringency conditions" refers to hybridization in 6×SSC at about 45° C., followed by one or more washes in 0.2×SSC, 0.1% SDS at 65° C. The nucleotide sequence constituting the probe polynucleotide can be prepared as one or more sequences consisting of arbitrary but at least consecutive 20 nucleotides, preferably at least 30 consecutive nucleotides, for example, consecutive 40, 60 or 100 nucleotides selected from the above-mentioned nucleotide sequences.

Further, based on the information on the above nucleotide sequences, PCR primers can be designed from regions exhibiting high homology. The gene encoding nitrile hydratases can be isolated from various organisms by PCR using such primers and chromosomal DNA or cDNA as a template.

In the method of the present invention, it is possible to use not only the natural enzyme but also an enzyme comprising the amino acid sequence of the natural enzyme in which one or more amino acids have been substituted, deleted, and/or inserted, when the enzyme can form the protein complex having the above-mentioned physicochemical properties (a) and (b) or (1) to (7). One skilled in the art can modify the structure of the polypeptide, for example, via introducing mutations of appropriate substitutions, deletions, insertions and/or additions by site-specific mutagenesis (Nucleic Acid Res. 10, pp. 6487 (1982); Methods in Enzymol. 100, pp. 448 (1983); Molecular Cloning 2nd Edt., Cold Spring Harbor Laboratory Press (1989).); PCR, A Practical Approach IRL Press pp. 200 (1991)) and such. Further, amino acid mutations can be generated in nature. Thus, not only the enzyme having artificial amino acid mutations but also the enzyme containing spontaneous amino acid mutations can be used in the method of the present invention.

The number of amino acids that are mutated is not particularly restricted, as long as the enzyme can form the protein complex having the above-mentioned physicochemical properties (a) and (b) or (1) to (7). Normally, it is within 50 amino acids, preferably within 30 amino acids, more preferably within 10 amino acids, and even more preferably within 3 amino acids. The site of mutation may be any site, as long as the enzyme can form the protein complex having the above-mentioned physicochemical properties (a) and (b) or (1) to (7).

An amino acid substitution is preferably mutated into different amino acid(s) in which the properties of the amino acid side-chain are conserved. A "conservative amino acid substitution" is a replacement of one amino acid residue belonging to one of the following groups having a chemically similar side chain with another amino acid in the same group. Groups of amino acid residues having similar side chains have been defined in the art. These groups include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In addition in the method of the present invention, the gene encoding a polypeptide having homology to the amino acid sequence of each subunit of nitrile hydratase can also be used for the present invention, when the product can form the protein complex having the above-mentioned physicochemical properties (a) and (b) or (1)-(7). The genes can be obtained by using protein homology search. Such homology search can be carried out, for example, by using the following publicly known databases:

Amino acid sequence databases for protein such as SWISS-PROT and PIR,

DNA databases such as DNA Databank of JAPAN (DDBJ), EMBL and GenBank,

Databases of amino acid sequences deduced from DNA sequences, and,

Programs for homology search such as FASTA program and BLAST program.

Further, database search services using the programs for searching the above databases are also available on Internet. The nitrile hydratase to be used in the present invention can be found by using this type of service.

A polypeptide having at least 85%, preferably 90% or higher, more preferably 95% or higher identity to the amino acid sequences of SEQ ID NO: 2 (α-subunit) or SEQ ID NO: 4 (β-subunit) is a preferred polypeptide of the present invention constituting the nitrile hydratase to be used in the present invention. As used herein, "percent identity" means, for example, the value of percent identity in "Positive" using BLAST program. Specifically, "percent identity" of two amino acid sequences or of two nucleic acids is determined using the algorithm of Karlin and Altschul (Proc. Natl. Acad. Sci. USA 87: 2264-2268, 1990) modified as in Karlin and Altschul (Proc. Natl. Acad. Sci. USA 90:5873-5877, 1993). Such an algorithm is incorporated into the NBLAST and XBLAST programs of Altschul et al. (J. Mol. Biol. 215: 403-410, 1990). BLAST nucleotide searches are performed with the NBLAST program, score=100, wordlength=12. Homology search of protein can readily be performed, for example, in DNA Databank of JAPAN (DDBJ), by using the FASTA program, BLAST program, etc. BLAST protein searches are performed with the XBLAST program, score=50, wordlength=3. Where gaps exist between two sequences, Gapped BLAST is utilized as described in Altsuchl et al. (Nucleic Acids Res. 25: 3389-3402, 1997). When utilizing BLAST and Gapped BLAST programs, the default parameters of the respective programs (e.g, XBLAST and NBLAST) are used.

In the present invention, when the protein complex is intended to be prepared by using mutant α-subunit comprising the amino acid sequence of SEQ ID NO: 2 and mutant β-subunit comprising the amino acid sequence of SEQ ID NO: 4 both of which have mutations in their amino acid sequences, either or both of them may be mutant polypeptides. Further, the subunits of different origins can be combined with each other to form the protein complex of the present invention. When one of the two subunits is intended to be a mutant, it should be selected to be capable of constituting the protein complex, which has the above-mentioned physicochemical properties (1) and (2), with the other subunit.

Further, when both α-subunit and β-subunit are intended to be mutants, one mutant is combined with the other, and mutants capable of constituting the protein complex that has the above-mentioned physicochemical properties (i) and (ii) are selected as well. In this case, first, a mutant subunit is tested to assess whether it gives the required physicochemical properties in combination with the other subunit having the wild-type amino acid sequence when the result is positive, another mutant, which gives the required physicochemical properties, is selected for the partner subunit that is used in combination with the first mutant; thus the mutants are readily selectable. The desirable mutants of the present invention have the above-mentioned physicochemical properties (a) and (b) or (1)-(7) as well as the above-mentioned physicochemical properties (i) and (ii).

Preferable enzymatically active material of the present invention includes a transformant of homologous or heterogonous host expressing the gene encoding nitrile hydratase, which has been prepared by genetic recombination techniques and treated products thereof.

There is no limitation on the organism to be used for the transformation to express the nitrile hydratase gene of the present invention, when the organism can be transformed with the recombinant vector containing polynucleotides encoding the respective subunits constituting the protein complex having the nitrile hydratase activity and can express the nitrile hydratase activity. The polynucleotides encoding the respective subunits can be retaining in a single vector. The polynucleotides for the respective subunits can also inserted separately in two types of vectors; the protein complex of the present invention can be expressed by the co-transformation of the vectors. Further, it is possible to obtain the protein complex of interest in vitro by combining the transformants each of which expresses a single subunit of the two. Available microorganisms are those for which host-vector systems are available and include, for example:

bacteria such as the genus *Escherichia*, the genus *Bacillus*, the genus *Pseudomonas*, the genus *Serratia*, the genus *Brevibacterium*, the genus *Corynebacterium*, the genus *Streptococcus*, and the genus *Lactobacillus*;

actinomycetes such as the genus *Rhodococcus* and the genus *Streptomyces*;

yeasts such as the genus *Saccharomyces*, the genus *Kluyveromyces*, the genus *Schizosaccharomyces*, the genus Zygosaccharomyces, the genus Yarrowia, the genus Trichosporon, the genus Rhodosporidium, the genus Pichia, and the genus Candida; and, fungi such as the genus Neurospora, the genus Aspergillus, the genus Cephalosporium, and the genus Trichoderma, etc.

Procedure for preparation of a transformant and construction of a recombinant vector suitable for a host can be carried out by employing techniques that are commonly used in the fields of molecular biology, bioengineering, and genetic engineering (for example, see Sambrook et al., "Molecular Cloning", Cold Spring Harbor Laboratories). In order to express the gene encoding nitrile hydratase of the present invention in a microorganism, it is necessary to introduce the polynucleotide into a plasmid vector or phage vector that is stable in the microorganism and to let the genetic information transcribed and translated. To do so, a promoter, a unit for regulating transcription and translation, is placed upstream of the 5'-end of the polynucleotide of the present invention, and preferably a terminator is placed downstream of the 3'-end of the polynucleotide. The promoter and the terminator should be functional in the microorganism to be utilized as a host. Available vectors, promoters, and terminators for the above-mentioned various microorganisms are described in detail in "Fundamental Course in Microbiology (8): Genetic Engineering", Kyoritsu Shuppan, specifically for yeasts, in "Adv. Biochem. Eng. 43, 75-102(1990)" and "Yeast 8, 423-488 (1992)."

For example, for the genus Escherichia, in particular, for Escherichia coli, available plasmids include pBR series and pUC series plasmids; available promoters include promoters derived from lac (derived from β-galactosidase gene), trp (derived from the tryptophan operon), tac and trc (which are chimeras of lac and trp), PL and PR of λ phage, etc. Available terminators are derived from trpA, phages, rrnB ribosomal RNA, etc. Among these, a vector pSE420D (described in Unexamined Published Japanese Patent Application No. (JP-A) 2000-189170), which is constructed by partially modifying the multicloning site of commercially available pSE420 (Invitrogen), can be preferably used.

For the genus Bacillus, available vectors are pUB110 series and pC194 series plasmids; the vectors can be integrated into host chromosome. Available promoters and terminators are derived from apr (alkaline protease), npr (neutral protease), amy (α-amylase), etc.

For the genus Pseudomonas, there are host-vector systems developed for Pseudomonas putida and Pseudomonas cepacia. A broad-host-range vector, pKT240, (containing RSF1010-derived genes required for autonomous replication) based on TOL plasmid, which is involved in decomposition of toluene compounds, is available; a promoter and a terminator derived from the lipase gene (JP-A Hei 5-284973) are available.

For the genus Brevibacterium, in particular, for Brevibacterium lactofermentum, available plasmid vectors include pAJ43 (Gene 39, 281 (1985)). Promoters and terminators used for Escherichia coli can be utilized without any modification for Brevibacterium.

For the genus Corynebacterium, in particular, for Corynebacterium glutamicum, plasmid vectors such as pCS11 (JP-A Sho 57-183799) and pCB101 (Mol. Gen. Genet. 196, 175(1984)) are available.

For the genus Streptococcus, plasmid vectors such as pHV1301 (FEMS Microbiol. Lett. 26, 239 (1985)) and pGK1 (Appl. Environ. Microbiol. 50, 94 (1985)) can be used.

For the genus Lactobacillus, plasmid vectors such as pAMβ1 (J. Bacteriol. 137, 614 (1979)), which was developed for the genus Streptococcus, can be utilized; and promoters that are used for Escherichia coli are also usable.

For the genus Rhodococcus, plasmid vectors isolated from Rhodococcus rhodochrous are available (J. Gen. Microbiol. 138, 1003 (1992)).

For the genus Streptomyces, plasmids can be constructed in accordance with the method as described in "Genetic Manipulation of Streptomyces: A Laboratory Manual" (Cold Spring Harbor Laboratories (1985)) by Hopwood et al. In particular, for Streptomyces lividans, pIJ486 (Mol. Gen. Genet. 203, 468-478, 1986), pKC1064 (Gene 103,97-99 (1991)), and pUWL-KS (Gene 165, 149-150 (1995)) are usable. The same plasmids can also be utilized for Streptomyces virginiae (Actinomycetol. 11, 46-53 (1997)).

For the genus Saccharomyces, in particular, for Saccharomyces cerevisiae, YRp series, YEp series, YCp series, and YIp series plasmids are available; integration vectors (refer EP 537456, etc.) which are integrated into chromosome via homologous recombination with multicopy-ribosomal genes, allow to introduce a gene of interest in multicopy and the gene incorporated is stably maintained in the microorganism; and thus, these types of vectors are highly useful. Available promoters and terminators are derived from genes encoding ADH (alcohol dehydrogenase), GAPDH (glyceraldehyde-3-phosphate dehydrogenase), PHO (acid phosphatase), GAL (β-galactosidase), PGK (phosphoglycerate kinase), ENO (enolase), etc.

For the genus Kluyveromyces, in particular, for Kluyveromyces lactis, available plasmids are those such as 2-μm plasmids derived from Saccharomyces cerevisiae, pKD1 series plasmids (J. Bacteriol. 145, 382-390(1981)), plasmids derived from pGKl1 and involved in the killer activity, KARS (Kluyveromyces autonomous replication sequence) plasmids, and plasmids (refer EP 537456, etc.) capable of being integrated into chromosome via homologous recombination with the ribosomal DNA. Promoters and terminators derived from ADH, PGK, and such are available.

For the genus Schizosaccharomyces, it is possible to use plasmid vectors comprising ARS (autonomous replication sequence) derived from Schizosaccharomyces pombe and auxotrophy-complementing selectable markers derived from Saccharomyces cerevisiae (Mol. Cell. Biol. 6, 80 (1986)). Promoters such as ADH promoter derived from Schizosaccharomyces pombe are usable (EMBO J. 6, 729 (1987)) In particular, pAUR224 is commercially available from TaKaRa Shuzo.

For the genus Zygosaccharomyces, plasmids originating from those such as pSB3 (Nucleic Acids Res. 13, 4267 (1985)) derived from Zygosaccharomyces rouxii are available; it is possible to use promoters such as PHO5 promoter derived from Saccharomyces cerevisiae and GAP-Zr (Glyceraldehyde-3-phosphate dehydrogenase) promoter (Agri. Biol. Chem. 54, 2521 (1990)) derived from Zygosaccharomyces rouxii.

For the genus Pichia, host vector system where Pichia-derived genes involved in autonomous replication (PARS1 and PARS2) are used in Pichia pastoris and such has been developed (Mol. Cell. Biol. 5, 3376 (1985)), and thus high-density cultivation and strong promoters such as methanol-inducible AOX are usable (Nucleic Acids Res. 15, 3859 (1987)). A Host-vector system has been developed for Pichia angusta (previously called Hansenula polyorpha) among the genus Pichia. Usable vectors include Pichia angusta-derived genes (HARS1 and HARS2) involved in autonomous replication, but they are relatively unstable.

Therefore, multi-copy integration of the gene into a chromosome is effective (Yeast 7, 431-443 (1991)). Promoters of AOX (alcohol oxidase) and FDH. (formic acid dehydrogenase), which are induced by methanol and such, are also available. Another host vector system where *Pichia*-derived genes involved in autonomous replication (PARS1 and PARS2) are used in *Pichia pastoris* and such has been developed (Mol. Cell. Biol. 5, 3376 (1985)), and thus high-density cultivation and strong promoters such as methanol-inducible AOX are usable (Nucleic Acids Res. 15, 3859 (1987)).

For the genus *Candida*, host-vector systems have been developed for *Candida maltosa, Candida albicans, Candida tropicalis, Candida utilis*, etc. An autonomous replication sequence originating from *Candida maltosa* has been cloned (Agri. Biol. Chem. 51, 51,1587 (1987)), and a vector using the sequence has been developed for *Candida maltosa*. Further, a chromosome-integration vector with a highly efficient promoter unit has been developed for *Candida utilis* (JP-A Hei. 08-173170).

For the genus *Aspergillus, Aspergillus niger* and *Aspergillus oryzae* have intensively been studied among fungi, and thus plasmid vectors and chromosome-integration vectors are available, as well as promoters derived from an extracellular protease gene and amylase gene (Trends in Biotechnology 7, 283-287 (1989)).

For the genus *Trichoderma*, host-vector systems have been developed for *Trichoderma reesei*, and promoters such as that derived from an extracellular cellulase gene are available. (Biotechnology 7, 596-603(1989)).

There are various host-vector systems developed for plants and animals other than microorganisms; in particular, the systems include those of insect such as silkworm (Nature 315, 592-594(1985)), and plants such as rapeseed, maize, potato and such are preferably usable. The culture of transformant and purification of nitrile hydratase from the transformant can be carried out by methods known to one skilled in the art.

Polynucleotides encoding nitrile hydratase to be used as inserts in the vector of the present invention include, for example, any one of the above polynucleotides shown in (A)-(E) and any one of the above polynucleotides shown in (a)-(e).

The polynucleotides encoding α-subunit and β-subunit of nitrile hydratase in the vector of the present invention are preferably linked in tandem. The term. "preferably linked in tandem" means the linkage such that a common regulatory region directs the expression of these subunits. Such an arrangement is expected to enable more efficient expression of the subunits and more efficient formation of the protein complex having the enzymatic activity. Alternatively, the polynucleotides for the respective subunits can also be inserted separately in two types of vectors; the protein complex can be expressed by the co-transformation of the two vectors.

The present invention also relates to transformants of the present invention retaining the vector in an expressible manner. The vector of the present invention can be transformed into an arbitrary host, when the host can retain the vector in a functional form. Such a host that is usable for this purpose includes, for example, *E. coli*.

The nitrile hydratase of the present invention, microorganism producing the nitrile hydratase, protein complex of the present invention, transformant producing the protein complex and treated products thereof are useful for the method to produce amides using nitrile compounds as the substrates. Namely, the present invention provides a method for producing amides, the method comprising the step of recovering the amides by contacting nitrile compounds with the enzymatically active material selected from the group consisting of nitrile hydratase of the present invention, microorganism producing the nitrile hydratase, protein complex of the present invention, transformant producing the protein complex and processed products thereof.

As used herein, the term "nitrile hydratase" means an enzyme having the above-mentioned physicochemical properties (a) and (b) or enzyme having the above-mentioned physicochemical properties (1)-(7). Further, the microorganism capable of producing the enzyme includes the strain *Rhodococcus* sp. Cr4 from which the enzyme is derived, microorganisms belonging to the genus *Rhodococcus* producing the enzyme of the present invention and transformed host microorganism containing the polynucleotide encoding the enzyme. Further, the term "transformed host microorganism" means a host microorganism capable of expressing the polynucleotides (A)-(E) encoding the above-mentioned α-subunit and/or polynucleotides (a)-(e) encoding β-subunit. The above-mentioned host microorganism can produce the protein complex of the present invention consisting of α-subunit and β-subunit of the present invention.

Further, the treated product of microorganism specifically includes microorganism of which cell membrane permeability has been modified by the treatment with a detergent or organic solvent such as toluene, cell-free extract obtained by lysing the cells by the treatment with glass beads or enzyme and material partially purified from the extract, etc. Alternatively, the treated product of the enzyme includes the enzyme linked with insoluble carrier or with aqueous carrier molecule and the immobilized enzyme molecules prepared by immobilize entrapping, etc.

In the present invention, the enzymatically active material includes all materials having the enzymatic activity of nitrile hydratase of the present invention. Accordingly, as long as a material has the desired enzymatic activity, it is included in the enzymatically active material, regardless of its enzymatic purity and solubility.

The enzyme reaction constituting the amide-producing method of the present invention can be carried out by contacting the above-mentioned enzymatically active material with a reaction solution containing a nitrile compound as the substrate. Specifically, the enzymatically active material can be contacted with the substrate in an aqueous solvent, mixed solvent consisting of aqueous solvent and water-soluble organic solvent, or two-phase system with a water-insoluble solvent. The aqueous solvent includes buffers having the buffering action at neutral pH such as phosphate buffer and Tris-HCl buffer. Alternatively, when the pH changes can be within a desirable range during the reaction by using an acid and alkali, no buffer is needed. The organic solvent immiscible with water includes, for example, ethyl acetate, butyl acetate, toluene, chloroform, n-hexane and isooctane, etc. The reaction can be conducted in a mixed solvent, which consists of an aqueous solvent, and organic solvent such as ethanol, acetone, dimethylsulfoxide and acetonitrile.

In the two-phase system, the enzymatically active material is present in the aqueous phase in which the material is used without any other solvent or combined with water or a buffer. The substrate compound can be dissolved in an aqueous solvent such as water, buffer and ethanol, and supplied to the reaction system. In this case, along with the enzymatically active material, the substrate constitutes a single-phase reaction system. In addition, the reaction of the present invention can be carried out by using immobilized enzyme, membrane reactor, etc. Furthermore, the transformant of the present invention can be used in the form of the culture, cells separated from the culture medium by filtration, centrifugation or the like, or cells resuspended in buffer, water, or the like after they are separated by centrifugation and washed. The separated cells can be used in a state as they are recovered, as their disrupts, as treated with acetone or toluene, or as lyophilizate. When the enzyme is extracellularly produced, the culture medium of the transformant can also be used after it is separated from the transformant by the usual methods. Forms of contacting the enzymatically active material with the reaction solution are not limited to these Examples. The reaction solution means a solution consisting of the substrate dissolved in an appropriate solvent that provides suitable environment for the expression of enzymatic activity.

There is no limitation on the type of nitrile compound to be used in the method for producing amides using the nitrile hydratase of the present invention. For example, the following nitrile compounds can be used in the method of the present invention.

Saturated mononitriles;
acetonitrile, propionitrile, butyronitrile, isobutyronitrile, valeronitrile, isovaleronitrile, capronitrile, etc.

Saturated dinitriles;
malononitrile, succinonitrile, glutarnitrile, adiponitrile, etc.

α-aminonitriles;
α-aminopropionitrile, α-aminomethylthiobutyronitrile, α-aminobutyronitrile, aminoacetonitrile, etc.

Nitriles having carboxyl groups;
cyanoacetic acid, etc.

β-aminonitriles;
amino-3-propionitrile, etc.

Unsaturated nitrites;
acrylonitrile, methacrylonitrile, cyanoallyl, crotonitrile, etc.

Aromatic nitrites;
benzonitrile, o-, m- and p-chlorobenzonitrile, o-, m- and p-fluorobenzonitrile, o-, m- and p-nitrobenzonitrile, p-aminobenzonitrile, 4-cyanophenol, o-, m- and p-tolunitrile, 2,4-dichlorobenzonitrile, 2,6-dichlorobenzonitrile, 2,6-difluorobenzonitrile, anisonitrile, α-naphthonitrile, β-naphthonitrile, phthalonitrile, isophthalonitrile, terephthalonitrile, cyanobenzyl, phenylacetonitrile, etc.

α-hydroxynitriles.

In the present invention, particularly preferable nitrile compounds include α-hydroxynitrile compound. In the amide-producing method of the present invention, there is no limitation on the type of α-hydroxynitrile compound. More specifically, for example, the compound represented by the above formula (1) can be used.

In the formula, R represents, substituted or unsubstituted alkyl group, substituted or unsubstituted alkenyl group, substituted or unsubstituted cycloalkyl group, substituted or unsubstituted alkoxy group, substituted or unsubstituted aryl group, substituted or unsubstituted aryloxy group, substituted or unsubstituted saturated or unsaturated heterocyclic group. α-hydroxyamide can be produced from the α-hydroxynitrile compounds.

The heterocyclic group includes the groups having at least one of nitrogen, oxygen and sulfur as the heteroatom. Further, the substituent includes, for example, alkyl group, alkoxy group acyl group, aryl group, aryloxy group, halogens such as chloride and bromide, hydroxy group, amino group, nitro group, thiol group, etc.

Specifically, for example, the following compounds or substituted products thereof can be used. As used herein, the substituted product means compounds having the substituents as exemplified above.

Lactonitrile
α-hydroxy-n-propionitrile
α-hydroxy-n-butyronitrile
α-hydroxy-isobutyronitrile
α-hydroxy-n-hexyronitrile
α-hydroxy-n-heptyronitrile
α-hydroxy-n-octyronitrile
α,γ-dihydroxy-β,β-dimethylbutyronitrile
Acroleincyanohydrin
Methacrylaldehyde cyanohydrin
3-chlorolactonitrile
4-methylthio-α-hydroxybutyronitrile
α-hydroxy-α-phenylpropionyl In addition, the substrate compound having aromatic ring and heterocycle include the following exemplary compounds and substituted products thereof.

Mandelonitrile
2-thiophenecarboxyaldehyde cyanohydrin
2-pyridinecarboxyaldehyde cyanohydrin
2-pyrrolecarboxyaldehyde cyanohydrin
2-furaldehyde cyanohydrin
2-naphthylaldehyde cyanohydrin Many of the nitrile compounds represented by the α-hydroxynitrile compound of formula (1) are decomposed into aldehyde and hydrocyanic acid in a polar solvent. For example, the α-hydroxynitrile compound of formula (1) is converted to the aldehyde and hydrocyanic acid of the following formula (2).

R—CHO        (2)

Since a state of equilibrium is established among these compounds, the consumption of α-hydroxynitrile compound by enzyme reaction shifts the equilibrium toward the α-hydroxynitrile compound.

On the other hand, cyanide and aldehyde derived from hydrocyanic acid may give some damage to the enzyme polypeptide. Accordingly, previously known nitrile hydratases cannot hydrate sufficient amounts of α-hydroxynitrile compound due to their decreased enzymatic activity, and thus do not provide enough yields of the products. However, the nitrile hydratase of the present invention retains the enzymatic activity even in the presence of cyanide or aldehyde. Thus, the enzyme can utilize nitrile compounds generated from aldehydes and hydrocyanic acids as the substrate. Accordingly, by the inventive method for producing α-hydroxyamide, the compound of formula (1) can be supplied from the aldehyde compound and hydrocyanic acid represented by the following formula (2).

R—CHO        (2)

The amide-producing method of the present invention is preferably conducted in the presence of a divalent metal ion. The divalent metal ion contributes to the activity of nitrile hydratase of the present invention. The preferable divalent metal ions include nickel ion and cobalt ion. These ions can be added to the reaction solution as an appropriate aqueous salt. Specifically, the ion can be added as a chloride salt.

In the present invention, the hydration or hydrolysis of nitrile compound can be achieved by contacting the enzymatically active material of the present invention with a substrate compound, or a mixture of aldehyde and hydrocyanic acid represented by formula (2), which can be converted to a substrate compound in an aqueous solvent such as water or buffer. The reaction solution preferably contains divalent metal ions.

As used herein, the term "hydration" means the reaction where water molecules attaches to the nitrile group. Contrasted with "hydration", the term-"hydrolysis" means the reaction where, from a compound in which a substituent is linked with the nitrile group, the substituent is cleaved off by hydrolysis. Both reactions are included by the amide-producing method of the present invention.

There is no limitation on the concentration of substrate compound in the reaction solution. In order to prevent the inhibition of enzymatic activity by the substrate compound, the concentration can correspond to, for example, 0.1-10 w/w % in general, preferably 0.2-5.0 w/w %, in the case of α-hydroxynitrile. The substrate can be added once at the start of reaction, but it is preferable to add the substrate continuously or discontinuously to prevent the substrate concentration from being too high.

When the solubility of nitrile compound as the substrate in the aqueous solvent is too low, a detergent can be added to the reaction solution. 0.1-5.0 w/w % Triton X-100 or Tween 60 can be use as the detergent. To increase the substrate solubility, a mixed solvent containing an organic solvent can be used effectively. Specifically, for example, the reaction efficiency can be improved by adding methanol, ethanol, dimethylsulfoxide, and such. Alternatively, the reaction of the present invention can be achieved in an organic solvent insoluble with water or two-phase system consisting of aqueous solvent and organic solvent insoluble with water. The organic solvent immiscible with water that is usable includes, for example, ethyl acetate, butyl acetate, toluene, chloroform, n-hexane, cyclohexane, octane or 1-octanol, etc.

When the substrate concentration falls within the range as described above, the efficient enzymatic reaction can be achieved by using nitrile hydratase of the present invention at an enzyme concentration, for example, of 1 mU/mL-100 U/mL, preferably 100 MU/mL or higher. Further, when microorganism cells are used as the enzymatically active material, the amount of microorganism to be used relative to that of the substrate preferably ranges from 0.01 to 5.0 w/w % as dry cells. The enzymatically active material such as an enzyme and cells can be contacted with the substrate by dissolving or dispersing them in a reaction solution. Alternatively, it is possible to use the enzymatically active material immobilized by the techniques of chemical linking or entrapment. Further, the reaction can be carried out in a state where the substrate solution is isolated from the enzymatically active material, with a porous membrane, through which the substrate is permeable, but which limits the permeation of the enzyme molecule or the cells.

The reaction can be carried out typically at a temperature ranging from the freezing point to 50° C., preferably at 10-30° C., for 0.1-100 hours. There is no limitation on the pH of reaction solution, when the enzymatic activity can be maintained. Since the optimal pH of nitrile hydratase of the present invention ranges from 5.5 to 6.5, it is preferable to adjust the pH of reaction solution within this range.

Thus, the nitrile compound is converted to a corresponding amide by the hydration or hydrolysis action of the microorganism, and accumulates in the reaction solution. The produced amide can be recovered and purified from the reaction solution by appropriate methods. Specifically, for example, the amide can be recovered and purified by the combined use of typical methods such as ultrafiltration, concentration, column chromatography, extraction, treatment with activated charcoal, distillation, etc.

The present invention provides a method for stabilizing the activity of nitrile hydratase in the presence of the nitrile compound, where the method is characterized by coexistence of divalent metal ions. Further, the present invention provides a method for producing amide, the method comprising the step of reacting the nitrile hydratase to the nitrile compound in the presence of divalent metal ion and recovering the amide generated.

The present invention is based on the finding that the presence of divalent metal ion in the reaction system markedly suppresses the decrease in the enzymatic activity of nitrile hydratase activity. In the present invention, there is no limitation on the origin of nitrile hydratase. Namely, any enzyme can be used, when the enzyme has the activity of acting on and hydrating the nitrile group of nitrile compound, and converting the nitrile group to the amide group. The nitrile hydratase, which hydrates α-hydroxynitrile to the corresponding amide, is the preferred enzyme in the present invention.

It can be assumed that the divalent metal ion of the present invention achieves the effect of suppressing the decrease in the nitrile hydratase activity, for example, by the following mechanism: At first, the binding of metal ion to the cyanohydrin structure of substrate compound may enhance the enzyme reaction. Secondly, the binding of metal ion may prevent the dissociation of cyanohydrin. As a result, the concentration of cyanide ion is reduced in the reaction solution. As the reduced cyanide ion concentration lowers the inhibitory effect on the enzyme, the enzymatic activity is raised.

In any case, it is assumed that these phenomena are not specific to some particular nitrile hydratases but generally found in the uses of substrate compounds having the cyanohydrin structure. This is the reason why there is no limitation on the origin of nitrile hydratase to be used in the method for stabilizing the activity of nitrile hydratase of the present invention or method for producing amides.

Known enzymes capable of hydrating nitrile compounds to the corresponding amides include, for example, the enzymes derived form the following microorganism (see JP-A Hei 04-040899).

The genus *Rhodococcus*
The genus *Corynebacterium*
The genus *Pseudomonas*
The genus *Arthrobacter*
The genus *Alcaligenes*
The genus *Bacillus*
The genus *Bacteridium*
The genus *Micrococcus*
The genus *Brevibacterium*
The genus *Nocardia*.

More specifically, for example, microorganisms include the following:

*Rhodococcus rhodochrous* ATCC 33278
*Rhodococcus erythropolis* IFO 12320
*Corynebacterium nitrilophilus* ATCC 21419
*Pseudomonas* sp. SK87 (FERM P-11311)
*Arthrobacter* sp. HR1 (FERM BP-3323)
*Alcaligenes* sp. BC16-2 (FERM BP-3321)
*Rhodococcus* sp. HT40-6 (FERM P-11774)
Microorganisms described in JP-B Sho 62-21519.

Other microorganisms are publicly known and available from American Type Culture Collection (ATCC); Institute of Applied Microbiology (IAM), The University of Tokyo; Fermentation Research Institute, the Agency of Industrial Science and Technology; KAKEN PHARMACEUTICAL Co. (KCC); Institute for Fermentation, Osaka (IFO); and RESEARCH CENTER FOR PATHOGENIC FUNGI AND MICROBIAL TOXICOSES (IFM), The University of Chiba. In addition, the nitrile hydratase of the present invention that can be obtained from the above-mentioned *Rhodococcus* sp. Cr4 (FERM BP-6596) is also one of the preferred enzyme of the present invention.

There is no limitation on the nitrile compound to be used in the amide-producing method of the present invention. More specifically, the preferred substrates include, for example, compounds illustrated in the above description for the method for producing α-hydroxyamide with the nitrile hydratase of the present invention.

It is also possible to conveniently produce only either of the two optically active isomers of α-hydroxyamide or α-hydroxy acid, the enzyme capable of stereospecifically hydrating or hydrolyzing nitrites or a microorganism containing the enzyme is used in the reaction. Thus, by the method of the present invention, the stereospecific α-hydroxyamide or α-hydroxy acid can be obtained much more advantageously than by the previous methods producing it through the step of optical resolution or racemization.

In the present invention, the hydration or hydrolysis of nitrile compound is carried out, for example, by contacting the nitrile hydratase with the α-hydroxynitrile represented by formula (1) in an aqueous solvent such as water or buffer. When the nitrile hydratase to be used is resistant to cyanide and aldehyde, the reaction can also be carried out in the presence of the aldehyde and hydrocyanic acid represented by formula (2), which can be converted to α-hydroxynitrile. The nitrile hydratase may be a lysate of microorganism capable of producing the enzyme, crude enzyme, or products obtained by immobilizing the materials, in addition to the purified enzyme. Further, in the present invention, the divalent metal ion may be added in the reaction solution at a concentration of 0.1 mM-1 M, generally 0.5-100 mM, preferably 1-10 mM.

There is no limitation on the type of metal ion to be used in the present invention, when the ion can be effective for maintaining the activity of nitrile hydratase. For example, cobalt ion and nickel ion are preferred metal ions, which can keep the activity of nitrile hydratase high. These metal ions can be added as salts such as chloride salts in the reaction solution.

In the present invention, the reaction conditions can be adjusted appropriately depending on the properties of substrate compounds to be used in combination with the nitrile hydratase, in addition to the presence of divalent metal ion. There is no limitation on the type of substrate compound and reaction conditions to be used in the reaction. Specifically, for example, the reaction system can be adjusted based on the exemplary conditions illustrated for the method for producing the α-hydroxyamide using the above-mentioned nitrile hydratase of the present invention.

Any patents, patent applications, and publications cited herein are incorporated by reference.

Herein, "%" for concentration denotes weight per volume percent unless otherwise specified.

BRIEF DESCRIPTION OF THE DRAWINGS

FIG. 12 shows the organization of gene cluster in *Rhodococcus* sp. Cr4. The nucleotide sequences indicated by capital letters correspond to the ORFs. The names of subunits encoded the ORFs are shown at the right of the nucleotide sequences.

FIG. 13 shows the amino acid comparison between α-subunits of nitrile hydratase from *Rhodococcus* sp. Cr4 and *Rhodococcus rhodochrous* J1. Between *Rhodococcus* sp. Cr4 (top panel; CrNH-α) and *Rhodococcus rhodochrous* J1 (bottom panel; J1 L-a), identical amino acids are represented by an asterisk and distinct amino acids are represented by a space.

FIG. 14 shows the amino acid comparison between β-subunits of nitrile hydratase from *Rhodococcus* sp. Cr4 and *Rhodococcus rhodochrous* J1. Between *Rhodococcus* sp. Cr4 (top panel; CrNH-β) and *Rhodococcus rhodochrous* J1 (bottom panel; J1 L-β), identical amino acids are represented by an asterisk and distinct amino acids are represented by a space.

BEST MODE FOR CARRYING OUT THE INVENTION

Figure 1:
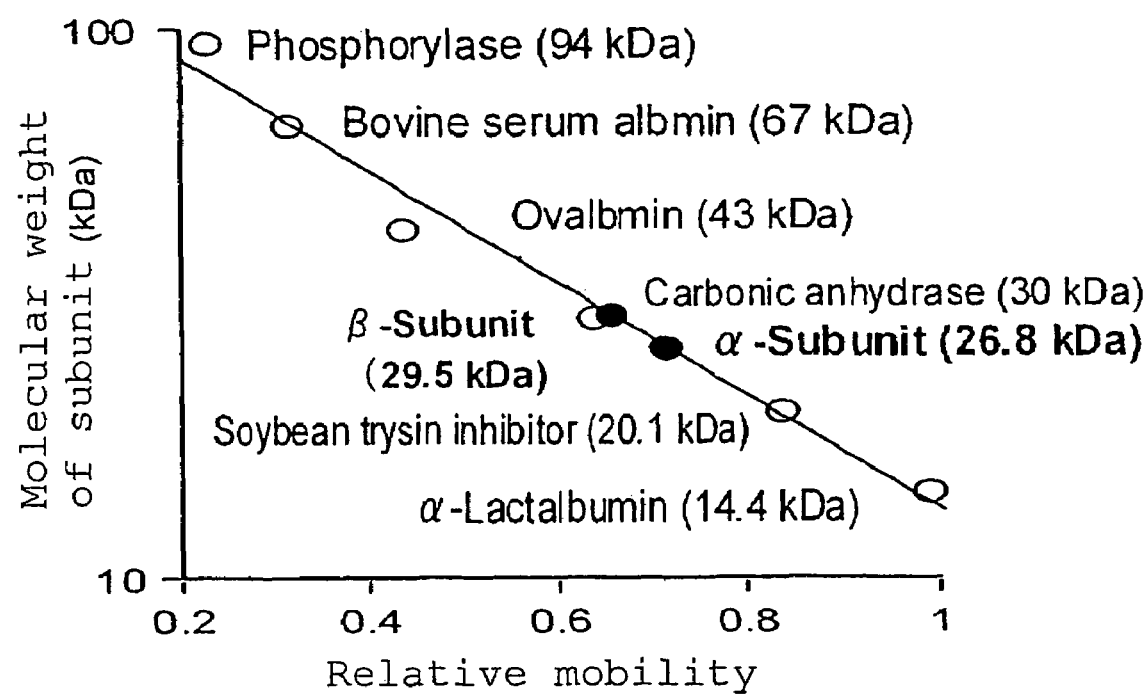
FIG. 1 shows the determination of molecular weight of nitrile hydratase of the present invention by SDS-PAGE. The abscissa indicates the relative mobility and the ordinate indicates the molecular weight (kDa).

The present invention is lustrated in detail below with reference to Examples, but is not to be construed as being limited thereto.

1. Assay Method for the Enzymatic Activity

The standard assay method for the nitrile hydratase activity used in the following Examples as follows. The standard composition of reaction solution for the enzyme reaction is shown in Tables 1 and 2. The enzyme reaction is initiated by adding 3-cyanopyridine or 2-hydroxy-4-methylthiobutyronitrile (HMBN) as the substrate compound. In the case of 3-cyanopyridine, incubation was continued at 20° C. for 10 minute, in the case of HMBN, at 20° C. for 15 minutes. When 3-cyanopyridine was used in the reaction, 0.1 ml of 2 N hydrochloric acid was added to the reaction and the mixture was shaken vigorously to stop the reaction; when HMBN was used in the reaction, 0.1 ml of the reaction solution was added to 0.9 ml of 0.1% (v/v) phosphoric acid and the mixture was shaken vigorously to stop the reaction. The reaction solution was analyzed by HPLC.

TABLE 1

| | |
|---|---|
| 10% (v/v) HMBN in 0.1 M KPB (pH 6.5) | 0.36 ml |
| 0.1 M KPB (pH 6.5) | 0.64 ml |
| Enzyme solution | 0.10 ml |
| 0.85% (w/v) NaClaq | 0.90 ml |
| Total volume | 2.00 ml |

10% (v/v) HMBN was added to initiate the reaction.
The mixture was incubated with shaking at 20° C. for 10 minutes.
0.1% (v/v) $H_3PO_4$ was added to stop the reaction.
Centrifugation.
HPLC analysis.

TABLE 2

| | |
|---|---|
| 0.3 M 3-cyanopridine | 1.00 ml |
| 0.1 M KPB (pH 7.0) | 0.50 ml |
| Enzyme solution | 0.10 ml |
| 0.85% (w/v) NaClaq | 0.90 ml |
| Total volume | 2.00 ml |

0.3 M 3-cyanopyridine was added to initiate the reaction.
The mixture was incubated with shaking at 20° C. for 3 minutes.
2 N HCl was added to stop the reaction.
Centrifugation.
HPLC analysis.

The conditions used in HPLC analysis of the reaction solution: The conditions used in HPLC analysis for HMBN are as follows:

| | |
|---|---|
| Column: | Spherisorb S5ODS2 (4.6 × 150 nm); |
| Mobile phase: | 0.1% (v/v) phosphoric acid/acetonitrile = 9/1; |
| Flow rate: | 1.0 ml/min.; |
| Detection: | UV 210 nm; |
| Column temperature: | 40° C. |

HPLC Analysis for the Enzymatic Activity:

The generated nicotinamide or HMBAm was quantified by HPLC, and the nitrile hydratase activity was calculated. The conditions of HPLC assay HMBAm were the same as that for HMBN. 1 U was defined as the enzyme quantity capable of producing 1 µmol nicotinamide with the standard composition of reaction solution at 20° C. for 1 minute; or 1 U was defined as the enzyme quantity capable of producing 1 µmol HMBAm with the standard composition of reaction solution at 20° C. for 1 minutes.

Protein Quantification:

The quantity of protein was determined according to Bradford method (Bradford, M., Anal, Biochem., 72, 248 (1976)) with a protein assay kit from Bio-Rad.

Reagent:

DEAE-Sephacel and Butyl-Toyopearl 650 M used was provided by Pharmacia; bovine serum albumin, from Bio-Rad; molecular weight marker for SDS-PAGE, from Pharmacia; molecular weight marker for HPLC, from Oriental yeast. Unless otherwise specified, other reagents used were commercially available special-grade reagents.

2. Culture Conditions

The pre-culture medium of the following composition was aliquoted in 5 ml into each test tube (25×200 mm); a silicone plug was placed in the tube, followed by sterilization by autoclaving. After the tube was cooled, a bacterial strain was inoculated with a platinum loop, and then cultured with shaking at 28° C. for two days.

| Pre-culture medium (pH 7.0): | |
|---|---|
| Polypeptone | 5.0 g |
| Meat extract | 5.0 g |
| NaCl | 2.0 g |
| Yeast extract | 0.5 g |
| Distilled water | 1.0 L |

Then, the pre-culture was transferred into 20-ml main-culture medium autoclaved in a 500-ml Sakaguchi flask. In the main culture, 0.75% (v/v) acetonitrile was added with a feeding needle after 24-hour culture, and then the incubation was continued with shaking at 33° C. for two days.

| Main-culture medium (pH 7.0): | |
|---|---|
| Acetamide | 7.5 g |
| Glucose | 10.0 g |
| C.S.L. | 10.0 g |
| Yeast extract | 1.0 g |
| $MgSO_4 7H_2O$ | 0.5 g |
| $K_2HPO_4$ | 1.0 g |
| $CoCl_2 6H_2O$ | 20.0 mg |
| Distilled water | 1.0 L |

3. Preparation of Cell-Free Extract

The bacterial cells corresponding to 500 ml of the culture liquid were suspended at a 5-times higher cell density in 50 mM phosphate buffer/44 mM n-butyric acid (pH 7.0). The suspended bacterial cells were homogenized with a sonicator 201 M (Kubota) with 150 W at 4° C. or a lower temperature for 60 minutes. Then, the culture was separated into the supernatant and precipitating fractions by centrifuge at 13,000 rpm for 20 minutes. The supernatant was used as cell-free extract for the following purification.

4. Ammonium-Sulfate Fractionation

Ammonium sulfate was added to the cell-free extract at 30% saturation. The mixture was neutralized to pH 7.0 with 10%(v/v) ammonium water, and then stirred at 4° C. for three hours. The solution was then fractionated into the supernatant and precipitating fractions by centrifuging at 13,000 rpm for 30 minutes. Ammonium sulfate was added to the supernatant fraction at 60% saturation. The mixture was neutralized to pH 7.0, and then stirred at 4° C. for three hours. The solution was then fractionated into the supernatant and precipitating fractions by centrifuging. Further, ammonium sulfate was added to the supernatant fraction at 80% saturation. After stirred, the solution was fractionated into the supernatant and precipitating fractions. The respective precipitates were suspended in 10 mM phosphate buffer/44 mMn-butyric acid (pH 7.0). The solutions were dialyzed three times against the same buffer. Then the activity was assayed.

5. DEAE-Sephacel Column Chromatography

The enzyme solution, which had been sufficiently dialyzed against the same buffer, loaded onto a column (φ13× 216 mm) of DEAE-Sephacel sufficiently equilibrated with 10 mM phosphate buffer/44 mM n-butyric acid (pH 7.0). The column was then washed with the same buffer. Then, elution was carried out with the following elution buffer, and the enzymatic activity in the fractions was assessed. The nitrile hydratase activity was found in the fractions of No.74-80 when eluted with 10 mM phosphate buffer/44 mM n-butyric acid (pH 7.0)/0.3 M KCl. The volume of each elution buffer used was approximately 3 times as much as-the volume of carrier.

10 mM phosphate buffer/44 mM n-butyric acid (pH 7.0)/0.1 M KCl 10 mM phosphate buffer/44 mM n-butyric acid (pH 7.0)/0.2 M KCl 10 mM phosphate buffer/44 mM n-butyric acid (pH 7.0)/0.3 M KCl 10 mM phosphate buffer/44 mM n-butyric acid (pH 7.0)/0.4 M KCl

6. Column Chromatography with Butyl-Toyopearl 650 M

A column (φ11×89 mm) containing Butyl-Toyopearl was sufficiently equilibrated with the buffer of 10 mM phosphate/44 mM n-butyric acid (pH 7.0) containing ammonium sulfate at 20% saturation. Ammonium sulfate was added to the enzyme solution at 20% saturation, and the mixture was stirred. The enzyme solution was loaded onto this column. The column was washed with the same buffer. Then, elution was carried out with the following elution buffer, and the enzymatic activity in the fractions was assessed. The nitrile hydratase activity was found in the fractions of No. 58-66 when eluted with 10 mM phosphate buffer/44 mM n-butyric acid (pH 7.0)/ammonium sulfate of 15% saturation. The volume of each elution buffer used was approximately 3 times as much as the volume of carrier.

10 mM phosphate buffer/44 mM n-butyric acid (pH 7.0)/ammonium sulfate of 15% saturation 10 mM phosphate buffer/44 mM n-butyric acid (pH 7.0)/ammonium sulfate of 10% saturation 10 mM phosphate buffer/44 mM n-butyric acid (pH 7.0)/ammonium sulfate of. 5% saturation

7. SDS-PAGE

The purified enzyme obtained was analyzed by SDS-PAGE. SDS-PAGE was carried out according to Laemmli's method (Laemmli, U.K.: Nature, 227, pp680, 1970). Namely, electrophoresis was performed in a 12% polyacrylamide slab gel with Tris/glycine buffer. An equal-volume mixture of enzyme solution and sample buffer was heat-treated at 90° C. for about 10 minutes. The gel was stained with Coomassie brilliant blue R-250; destaining was carried out with ethanol/acetic acid/dH$_2$O (2/3/6, by vol.). The result was shown in FIG. 1. The purified enzyme was revealed to consist of α-subunit (26.8 kDa) and β-subunit (29.5 kDa).

8. Gel Filtration by HPLC

Figure 2:
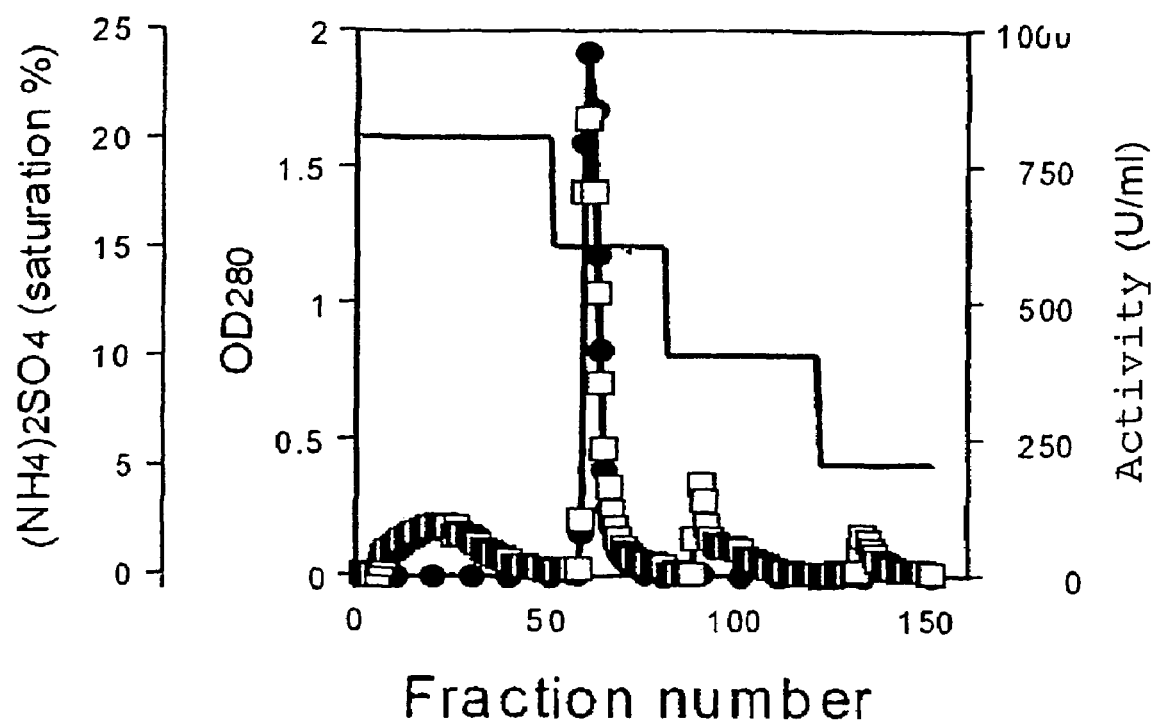
FIG. 2 shows an elution profile of nitrile hydratase of the present invention by column chromatography with butyl-Toyopearl 650M. White square (□) represents $OD_{280}$, closed circle (●) represents the activity and hyphen (-) represents $(NH_4)_2SO_4$.

The nitrile hydratase was purified according to the method as described above. First, the suspension of homogenized bacterial cells was fractionated into the supernatant and precipitating fractions by centrifugation. The activity was contained in the supernatant fraction, and thus the supernatant was used as a cell-free extract. The cell-free extract was fractionated with ammonium sulfate, and, as a result, the activity was contained in the fractions of which ammonium sulfate concentration is 30-60% saturation. The active fractions were subjected to column chromatography with DEAE-Sephacel. The active fractions (No. 74-80) eluted from the column of DEAE-Sephacel were collected, and then subjected to column chromatography with Butyl-Toyopearl 650 M. The active fractions (No. 0.58-66) eluted from the column of Butyl-Toyopearl 650 M were used as the purified enzyme (FIG. 2).

Finally, with respect to the nitrile hydratase of *Rhodococcus* sp. Cr4, the total protein content was 5.32 mg; specific activity, 477 U/mg.; yield, 44%; specific activity, 13.9 times (Table 3). The purified enzyme was assessed to be homogeneous by SDS-PAGE. The specific activity of finally purified enzyme was 880 U/mg for HMBN and 477 U/mg for 3-cyanopyridine used as the substrate under the standard conditions.

TABLE 3

| Step | Total protein (mg) | Total activity (U) | Specific activity (U/mg) | Purification (-fold) | Yield (%) |
|---|---|---|---|---|---|
| 1. Cell-free extract | 167 | 5740 | 34.4 | 1 | 100 |
| 2. (NH4)2SO4 fractionation | 56.6 | 5220 | 92.2 | 2.68 | 91 |
| 3. DEAE-Sephacel | 18.7 | 4030 | 215 | 6.25 | 70 |
| 4. Butyl-Toyopearl 650 M | 5.32 | 2540 | 477 | 13.9 | 44 |

1 U of the enzyme is defined as the amount to catalyze the production of 1 μmol nicotinamide from 3-cyanopyridine under the standard conditions during 1 minute.

Figure 3:
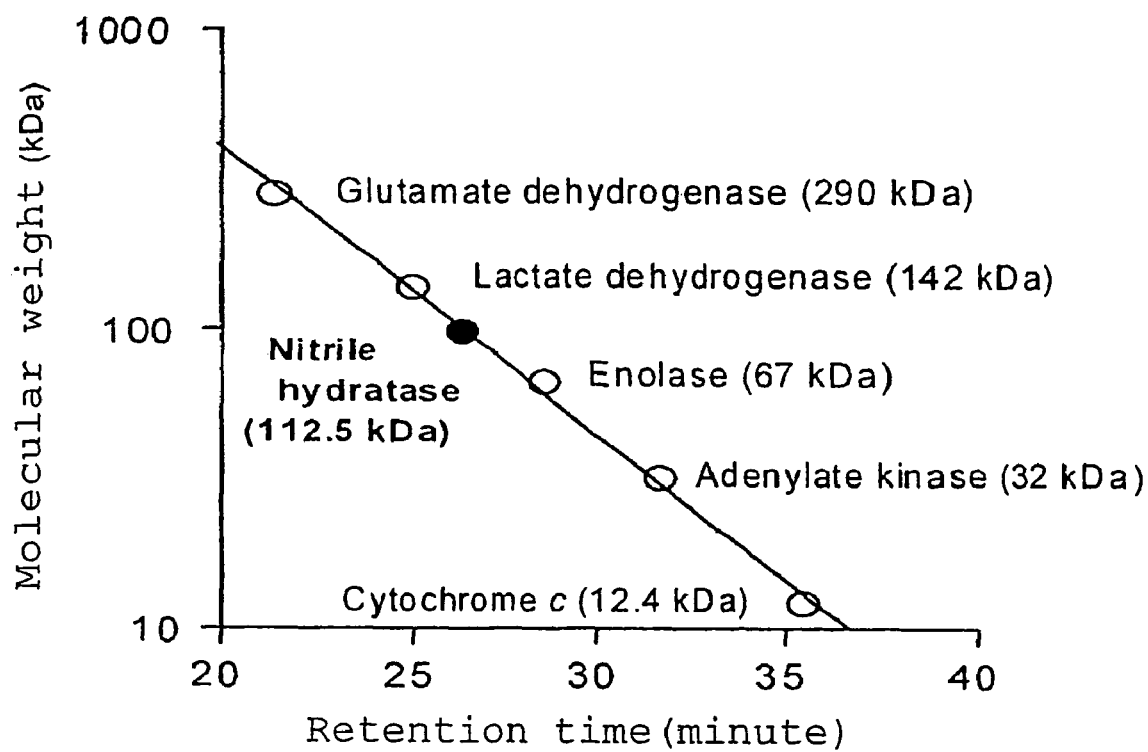
FIG. 3 shows the determination of molecular weight of nitrile hydratase of the present invention by gel filtration. The abscissa indicates retention time (minute) and the ordinate indicates the molecular weight (kDa).

About 2.3 μg of purified enzyme was analyzed by gel filtration under the conditions as shown in Table 4 to determine the molecular weight; the molecular weight of the enzyme in the natural state was deduced to be about 112.5 kDa, when it was calculated based on the retention time for the molecular weight marker (FIG. 3).

Gel Filtration by HPLC:

The conditions used for the HPLC analysis of nitrile hydratase for the molecular weight is shown in Table 4. The molecular weight marker used was from Oriental Yeast.

TABLE 4

| | |
|---|---|
| Column: | TSK gel G-3000 SW (0.75 × 60 cm) |
| Solvent: | 0.1 M KPB (pH 7.5) + 0.2 M KCl |
| Flow rate: | 0.7 ml/min |
| Injection: | 5 μl |
| Detection: | 280 nm |

9. The Effect of Substrate Concentration (Km Value)

Figure 4:
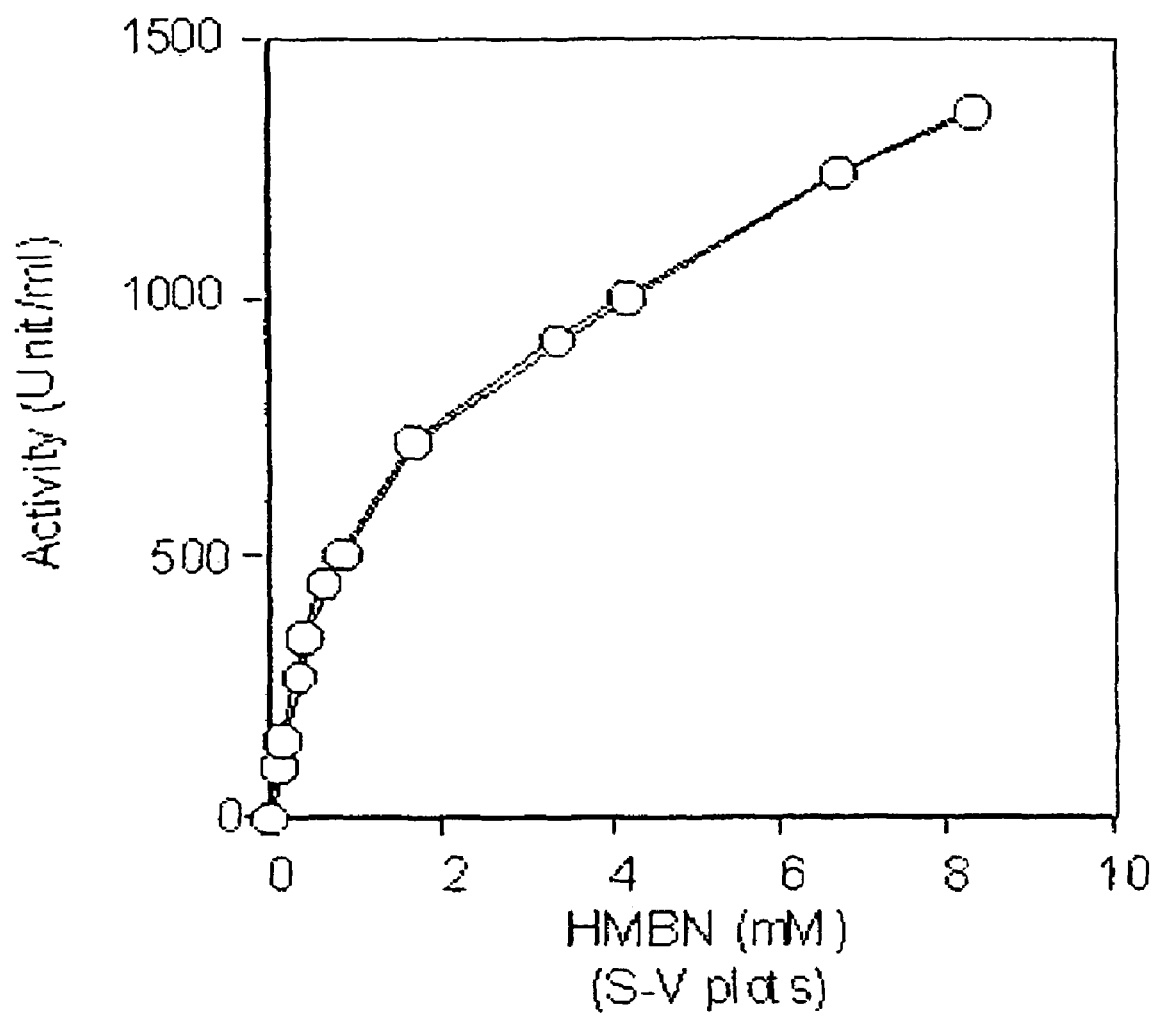
FIG. 4 shows the Km value of nitrile hydratase of the present invention for HMBN, which was determined with an S-V plot.
Figure 5:
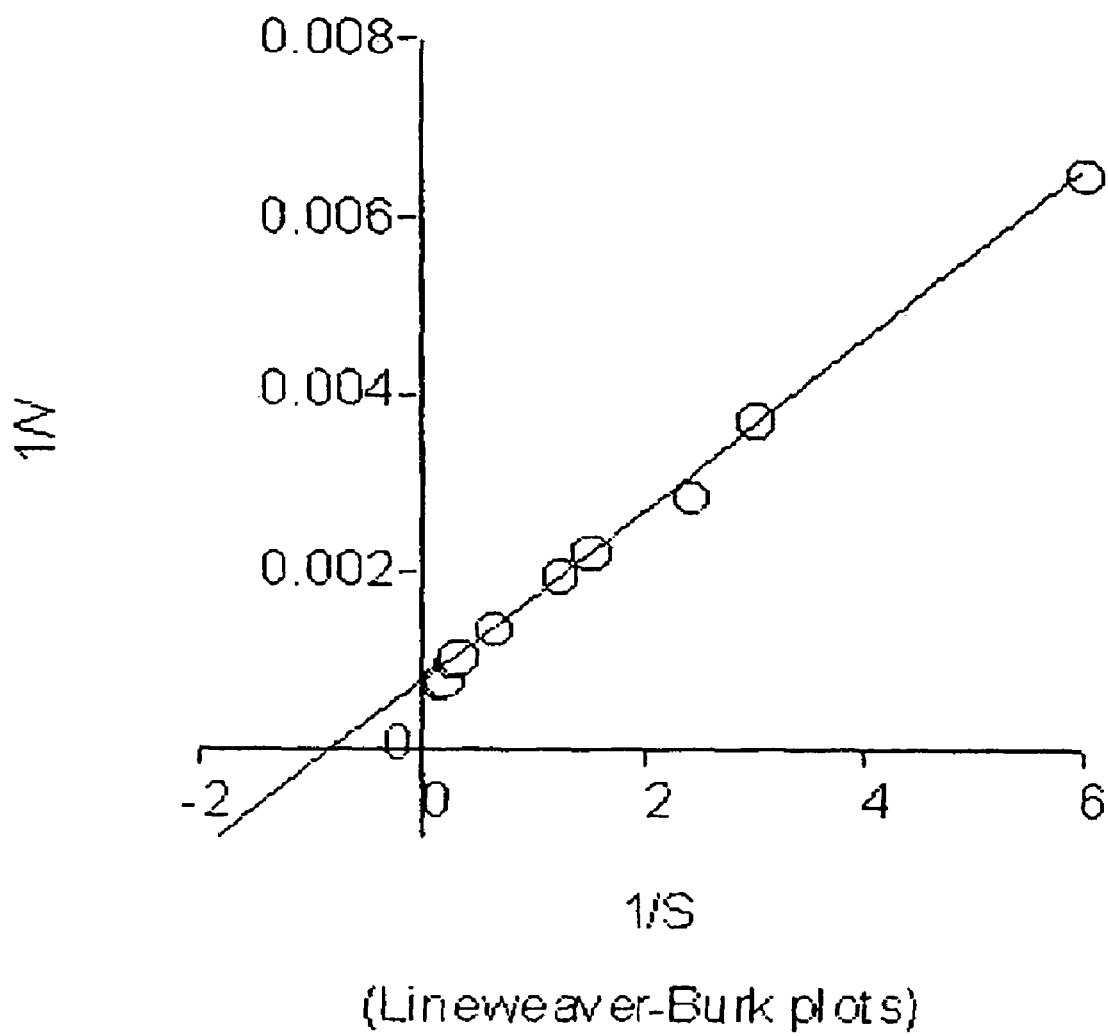
FIG. 5 the Km value of nitrile hydratase of the present invention for HMBN, which was determined with a Lineweaver-Burk plot.

The Km value for HMBN was determined from the S-V plot (FIG. 4) and Lineweaver-Burk plot (FIG. 5). 0.0585 U of the enzyme was added to solutions containing HMBN at various concentrations and the reactions were incubated at 20° C. for 15 minutes. The reactions were analyzed by HPLC. The Km value for HMBN was determined to be 1.43 mM from the Lineweaver-Burk plot, and this indicates that the enzyme has high affinity for HMBN.

Figure 6:
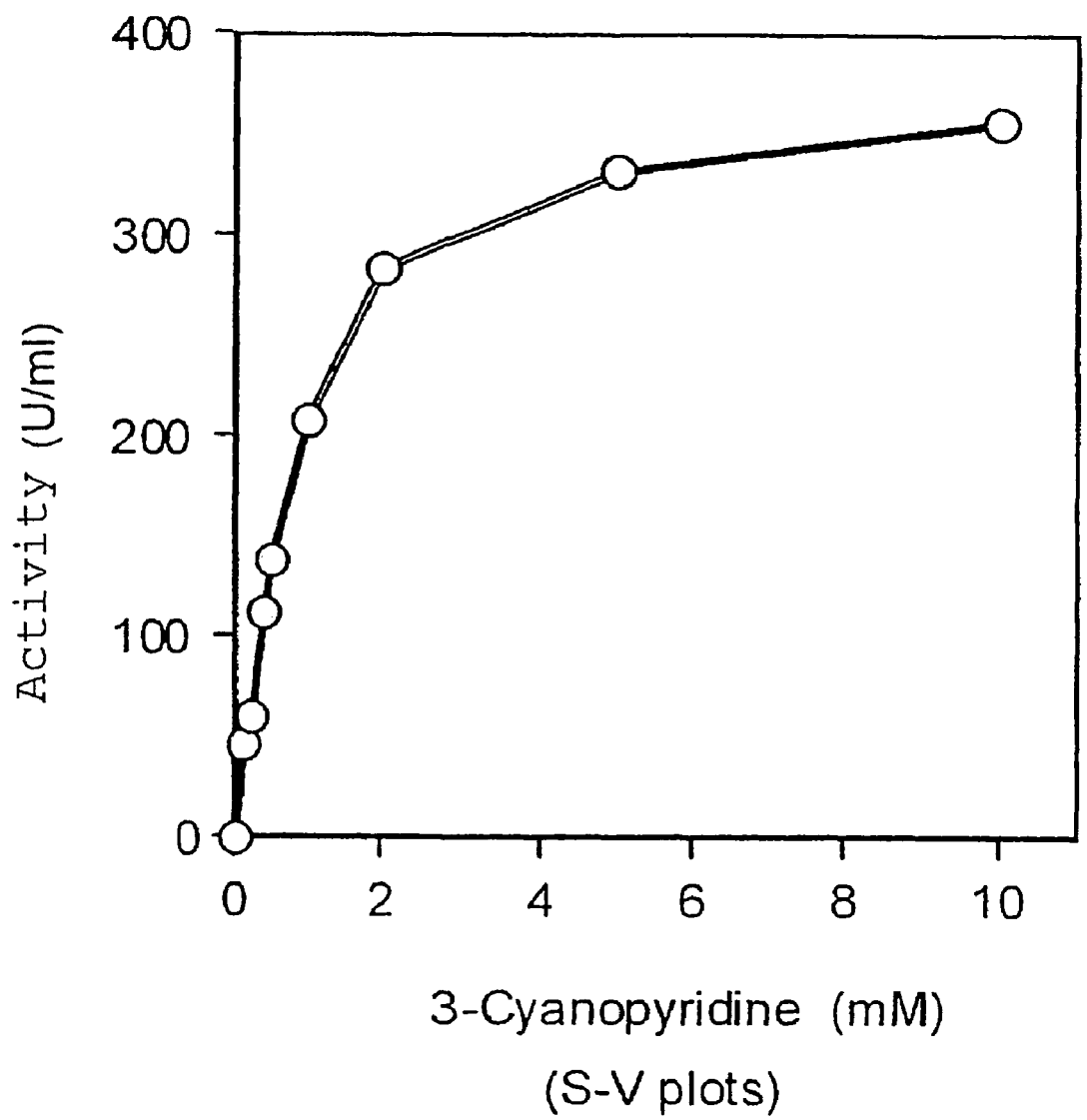
FIG. 6 shows the Km value of nitrile hydratase of the present invention for 3-cyanopyridine, which was determined with an S-V plot.
Figure 7:
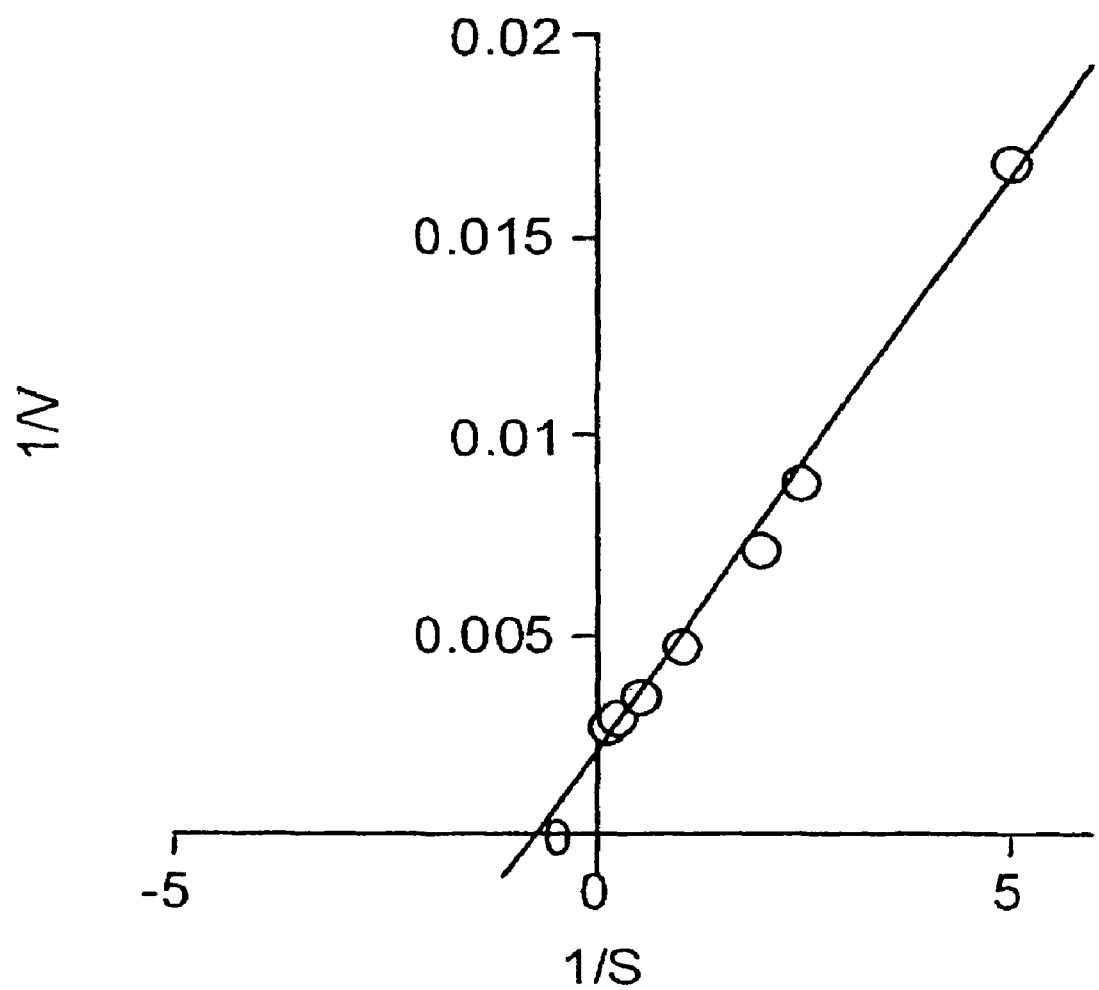
FIG. 7 shows the Km value of nitrile hydratase of the present invention for 3-cyanopyridine, which was determined with a Lineweaver-Burk plot.

In addition, the Km value for 3-cyanopyridine was determined from the S-V plot (FIG. 6) and Lineweaver-Burk plot (FIG. 7). Similarly, 0.0265 U of the enzyme was added to solutions containing 3-cyanopyridine at various concentrations and the reactions were incubated at 20° C. for 15 minutes. The reactions were analyzed by HPLC. The Km value for 3-cyanopyridine was determined to be 1.38 mM from the Lineweaver-Burk plot, and this indicates that the enzyme also has high affinity for 3-cyanopyridine.

10. The Effect of Temperature

Figure 8:
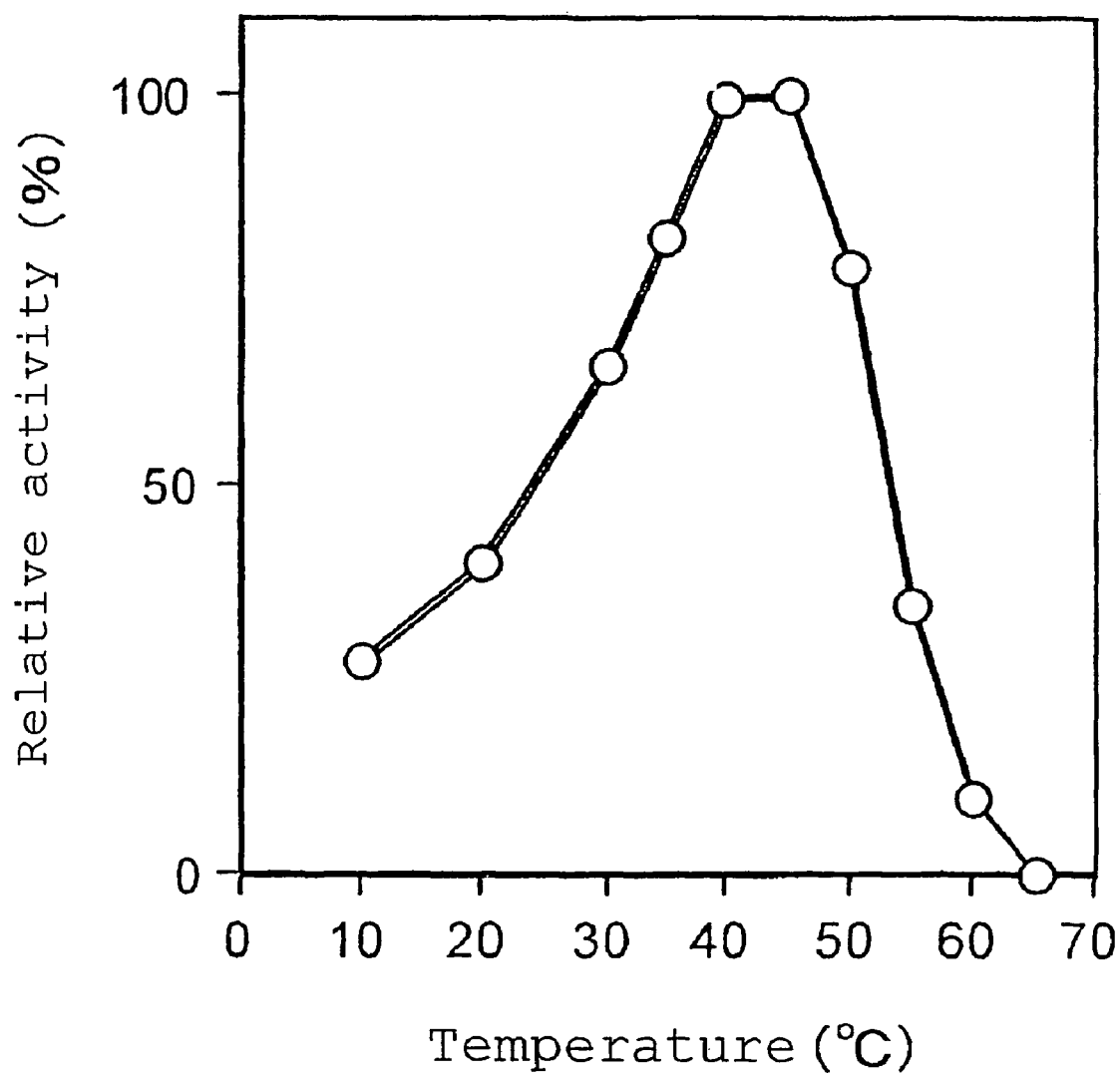
FIG. 8 shows the effect of temperature on the activity of nitrile hydratase of the present invention.
Figure 9:
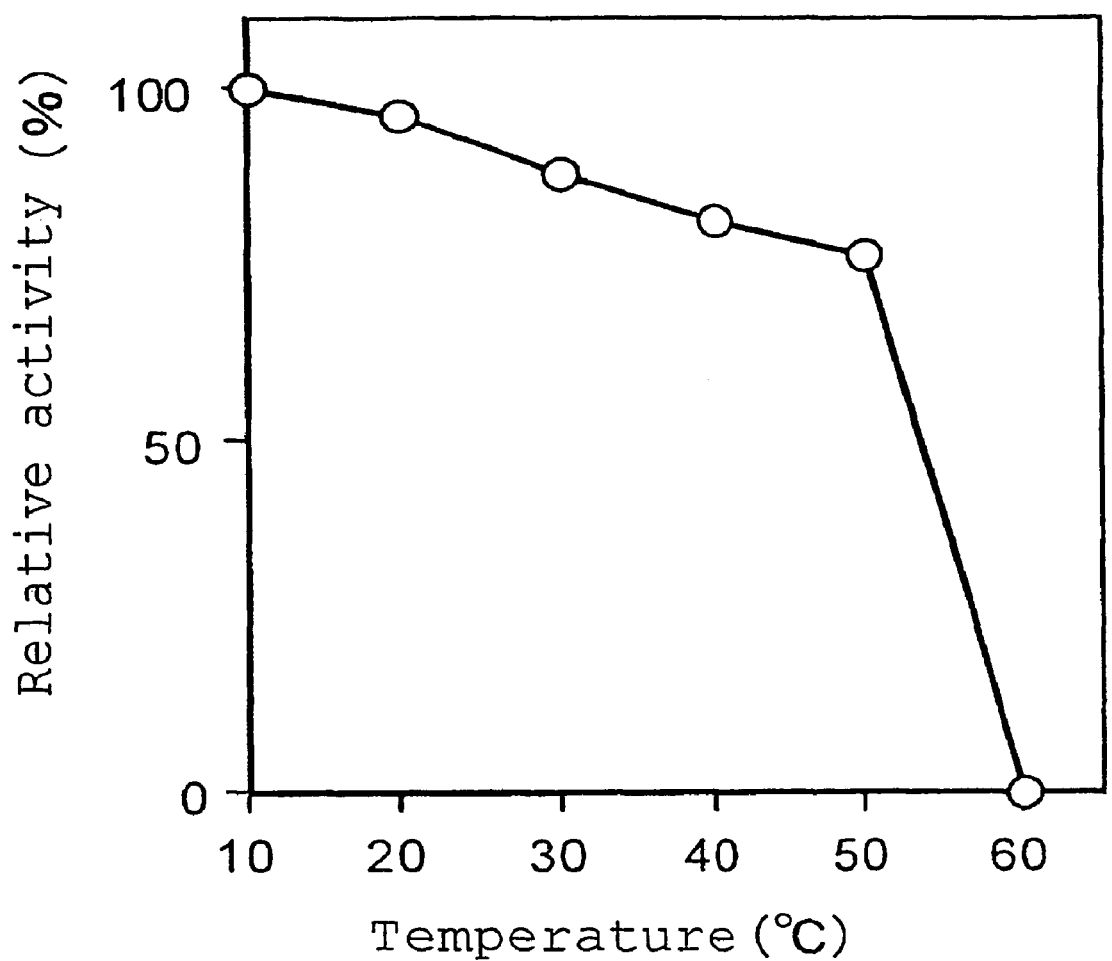
FIG. 9 shows the thermal stability of nitrite hydratase of the present invention.

The optimal temperature and thermal stability of the purified enzyme was evaluated. With the standard composition of reaction solution as shown in Table 1, 2.92 U enzyme was incubated at each temperature (10, 20, 30, 35, 40, 45, 50, 55, 60, or 65° C.) for 15 minutes to assess the optimal temperature (FIG. 8). The temperature, at which the reaction rate with the enzyme was maximized, was 45° C. Further, 2.92 U of the enzyme was heat-treated at each temperature (10, 20, 30, 40, 50, or 60° C.) for 30 minutes, and then the thermal stability was assessed under the standard reaction conditions. After the enzyme treated at 50° C., the remaining activity was 77% (FIG. 9).

11. The Effect of pH

Figure 10:
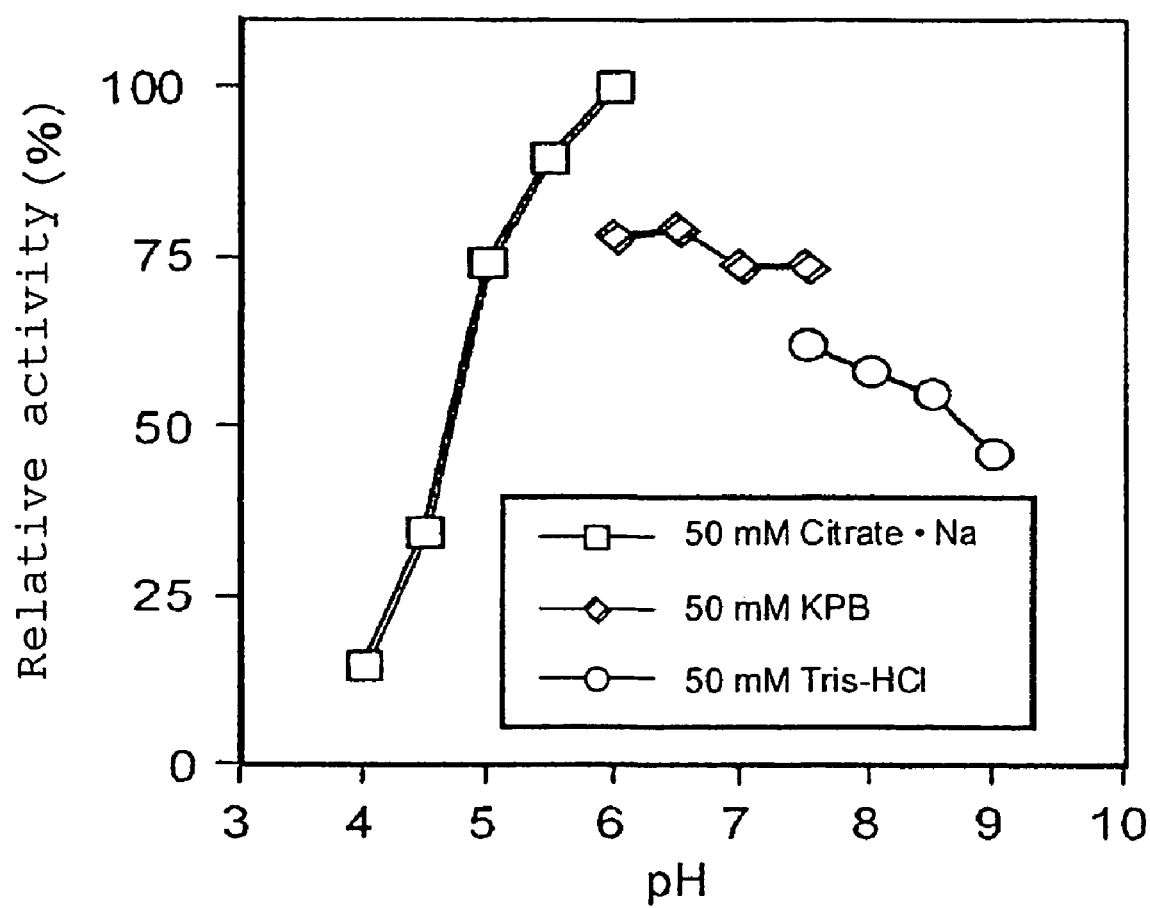
FIG. 10 shows the effect of pH on the activity of nitrile hydratase of the present invention.

The optimal pH and pH stability of the purified enzyme was evaluated. With the standard composition of reaction solution as shown in Table 1, 2.92 U enzyme was incubated in each buffer (buffer of sodium citrate or Tris-HCl at a final concentration of 50 mM), instead of phosphate buffer, at 20° C. for 15 minutes to determine the optimal pH. The optimal pH was 6.0 (FIG. 10).

Figure 11:
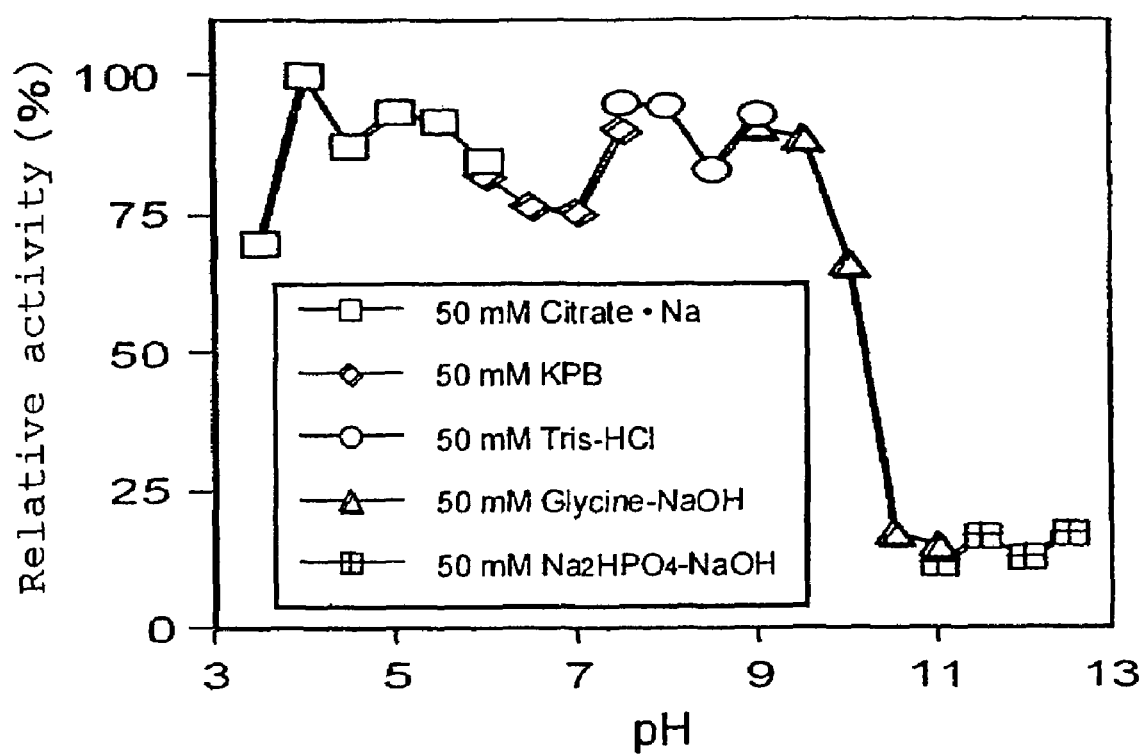
FIG. 11 shows the pH stability of the nitrile hydratase of the present invention.

Further, 2.92 U enzyme was incubated in each buffer (buffer of sodium citrate, phosphate buffer, Tris-HCl, Glycine/NaOH or $Na_2HPO_4$/NaOH at a final concentration of 50 mM) at 20° C. for 30 minutes, and then the remaining activity was assayed under the standard reaction conditions to assess the pH stability. After the enzyme treated at pH 4.0-9.0 for 30 minutes, the remaining activity was nearly 100% (FIG. 11).

12. Substrate specificity

The substrate specificity of the enzymewas examined. With the standard composition reaction solution shown in table 2, 2.92 U enzyme was incubated with various types of substrates, instead of 3-cyanopyridine; the generation of amides in the reaction solution was analyzed by HPLC. Thus, the relative activity was determined. The types of substrate compounds added, final concentrations thereof, reaction times, and HPLC conditions used for the analyses of products corresponding to the respective substrates are shown in Table 6. The HPLC conditions (1)-(9) are indicated next to Table 6.

The purified nitrile hydratase showed substrate specificity that was very similar to that of resting cell reaction; malononitrile, n-butyronitrile and 2-cyanopyridine were suitable substrates. The relative activity for HMBN was 154%, when the activity for 3-cyanopyridine was taken as 100% (Table 5).

TABLE 5

| Substrate | Relative activity (%) |
|---|---|
| 3-Cyanopyridine | 100 |
| 2-Cyanopyridine | 223 |
| 4-Cyanopyridine | 127 |
| Acrylonitrile | 114 |
| Methacrylonitrile | 93.7 |
| Crotononitrile | 87.4 |
| Acetonitrile | 14.6 |
| Propionitrile | 173 |
| HMBN | 154 |
| KCN | 0 |
| Malononitrile | 673 |
|  | 6.16 |
| 2-Cyanoacetamide | 46.3 |
| Cyanopyrazine | 114 |
| 3-Cyanopyridine* | 76.5 |

TABLE 5-continued

| Substrate | Relative activity (%) |
|---|---|
| n-Butyronitrile* | 379 |
| Isobutyronitrile* | 40.9 |
| n-Valeronitrile* | 118 |
| Isovaleronitrile* | 2.71 |
| n-Capronitrile* | 18.1 |
| 3-Indolylacetonitrile* | 2.33 |
| Benzonitrile* | 138 |
| o-Chlorobenzonitrile* | 58.6 |
| m-Chlorobenzonitrile* | 7.18 |
| p-Chlorobenzonitrile* | 28.4 |

The reaction was carried out at 20° C., and the amount of enzyme used was 2.92 U. The asterisk "*" indicates that methanol was added to enhance the substrate solubility (final conc.=20% v/v).

TABLE 6

| Substrate | Final concentration (mM) | Reaction time (min) | HPLC conditions |
|---|---|---|---|
| 3-Cyanopyridine | 150 | 15 | (1) |
| 3-Cyanopyridine* | 150 | 15 | (1) |
| 2-Cyanopyridine | 125 | 10 | (1) |
| 4-Cyanopyridine | 125 | 10 | (1) |
| Acrylonitrile | 250 | 3 | (5) |
| Methacrylonitrile | 150 | 5 | (1) |
| Crotononitrile | 150 | 5 | (1) |
| Acetonitrile | 250 | 10 | (4) |
| Propionitrile | 150 | 5 | (4) |
| n-Butyronitrile* | 150 | 10 | (2) |
| Benzonitrile* | 50 | 10 | (3) |
| o-Chlorobenzonitrile* | 25 | 5 | (3) |
| m-Chlorobenzonitrile* | 25 | 5 | (3) |
| p-Chlorobenzonitrile* | 25 | 5 | (3) |
| Malononitrile | 250 | 3 | (6) |
| Isobutyronitrile* | 150 | 10 | (7) |
| n-Valeronitrile* | 150 | 10 | (7) |
| Isovaleronitrile* | 150 | 10 | (7) |
| n-Capronitrile* | 150 | 10 | (9) |
| Cyanopyrazine | 150 | 10 | (8) |
| 3-Indolylacetonitrile* | 50 | 5 | (9) |

The conditions for HPLC were as follows:

(1) Column: Waters Spherisorb 5 μODS2 (4.6×150 mm);
Solvent: 10 mM $KH_2PO_4$(pH 2.8)/acetonitrile (v/v)=9:1;
Flow rate: 1.0 ml/min;
Detection: 230 nm;
Injection volume: 5 μl.

(2) Column: Waters Spherisorb 5 μODS2 (4.6×150 mm);
Solvent: 10 mM $KH_2PO_4$(pH 2.8)/acetonitrile (v/v)=9:1;
Flow rate: 1.0 ml/min;
Detection: 230 nm;
Injection volume:5 μl.

(3) Column: Waters Spherisorb 5 μODS2 (4.6×150 mm);
Solvent: 5 mM $KH_2PO_4$ (pH 2.8)/acetonitrile (v/v)=12:7;
Flow rate: 1.0 ml/min;
Detection: 230 nm;
Injection volume: 5 μl.

(4) Column: Waters Spherisorb 5 μODS2 (4.6×150 mm);
Solvent: 10 mM $KH_2PO_4$(pH 2.5)/acetonitrile (v/v)=99:1;
Flow rate: 1.0 ml/min;
Detection: 210 nm;
Injection volume: 5 μl.

(5) Column: Waters Spherisorb 5 μODS2 (4.6×150 mm);
Solvent: 10 mM $KH_2PO_4$(pH 2.5)/acetonitrile (v/v)=99:1;
Flow rate: 1.0 ml/min;
Detection: 230 nm;
Injection volume: 5 μl.
(6) Column: Spherisorb S5ODS2 (4.6×150 mm)
Solvent: 0.1% (v/v) phosphate/acetonitrile (v/v)=99:1;
Flow rate: 1.0 ml/min;
Detection: 210 nm;
Injection volume: 5 μl.
(7) Column: Spherisorb S5ODS2 (4.6×150 mm);
Solvent: 0.1% (v/v) phosphate/acetonitrile (v/v)=9:1;
Flow rate: 1.0 ml/min;
Detection: 210 nm;
Injection volume: 5 μl;
Temperature: 40° C.
(8) Column: Spherisorb S5ODS2 (4.6×150 mm);
Solvent: 0.1%(v/v) phosphate/acetonitrile (v/v)=9:1;
Flow rate: 1.0 ml/min;
Detection: 230 nm;
Injection volume: 5 μl
Temperature: 40° C.
(9) Column: Spherisorb S5ODS2 (4.6×150 mm);
Solvent: 5 mM $KH_2PO_4$ (pH 2.8)/acetonitrile (v/v)=12:7;
Flow rate: 1.0 ml/min;
Detection: 210 nm;
Injection volume: 5 μl;
Temperature: 40° C.

13. The Effect of Inhibitors on the Enzymatic Activity

Inhibitors to the enzyme were studied. With the standard composition of reaction solution shown in Table 1, various inhibitors were added at a final concentration 1.0 mM or 0.1 mM to the solutions containing 2.92 U enzyme; after the mixtures were incubated at 20° C. for 10 minutes, the reaction was carried out for 15 minutes. The enzyme activity was markedly inhibited by carbonyl reagents such as phenyl hydrazine and hydroxylamine (Table 7).

TABLE 7

The effects of various compounds on the nitrile hydratase activity

| Compound (1.0 mM) | Relative activity (%) |
| --- | --- |
| Free | 100 |
| Iodoacetate | 97.0 |
| N-Ethylmaleimide | 101 |
| p-Chloromercuribenzoate | 97.7 |
| 5-5'-Dithiobis (0.1 mM) | 99.1 |
| Hydroxylamine | 62.1 |
| Phenylhydrazine | 8.19 |
| Cysteamine | 106 |
| D-Cycloserine | 94.8 |
| EDTA | 101 |
| Tiron | 132 |
| Diethyldithiocarbamate | 97.7 |
| Urea | 95.7 |
| $NaN_3$ | 98.5 |
| Dithiothreitol | 93.4 |

The enzyme was incubated with various compounds at 20° C. for 20 minutes, and the enzymatic activity was assayed.

14. The Effect of Metal Ion on the Enzymatic Activity

The effect of metal ion the enzyme reaction was studied. With the standard composition of reaction solution shown in Table 1, various metal ions were added at a final concentration 1.0 mM to the solutions containing 2.92 U enzyme; after the mixtures were incubated at 20° C. for 10 minutes, the reaction was carried out for 15 minutes. The enzyme activity was markedly inhibited by heavy metal ions such as $Ag^+$ and $Hg^{++}$ ions capable of specifically interacting with SH groups.

On the contrary, the addition of $Ni^{++}$ or $Co^{++}$ ion enhanced the enzymatic activity (Table 8).

TABLE 8

The effect of metal ion on the nitrile hydratase activity

| Metal (1.0 mM) | Relative activity (%) |
| --- | --- |
| Free | 100 |
| $CaCl_2$ | 96.4 |
| $MnCl_2$ | 96.7 |
| $NiCl_2$ | 196 |
| $CoCl_2$ | 154 |
| $ZnSO_4$ | 84.1 |
| $CuSO_4$ | 109 |
| $FeSO_4$ | 78.9 |
| $FeCl_3$ | 100 |
| $AgNO_3$ | 7.85 |
| $HgCl_2$ | 7.48 |

The enzyme was incubated with a metal ion at 20° C. for 10 minutes, and the enzymatic activity was assayed.

15. The Effect of Coexisting $Ni^{++}$ and $Co^{++}$ Ions on the Enzymatic Activity It was revealed that the addition of $Ni^{++}$ or $Co^{++}$ ion to the reaction system enhanced the enzymatic activity. With the standard composition of reaction solution shown in Table 1, $Ni^{++}$ or $Co^{++}$ ion was added at a concentration of 0-8.0 mM to a solution containing 2.92 U enzyme; its effect on the enzymatic activity was studied. When $Ni^{++}$ or $Co^{++}$ ion was added at a concentration of 1.0-2.0 mM, the enzymatic activity was enhanced twice or 1.5 times. As the metal ions were added at higher concentration than above-mentioned one, the enhancement was impaired (Tables 9 and 10).

TABLE 9

The effect of cobalt ion on the nitrile hydratase activity

| $CoCl_2$ (mM) | Relative activity (%) |
| --- | --- |
| 0 | 100 |
| 0.5 | 129 |
| 1.0 | 150 |
| 2.0 | 153 |
| 4.0 | 143 |
| 6.0 | 136 |
| 8.0 | 127 |

The enzyme incubated with nickel ion at 20° C. for five minutes, and the enzymatic activity was assayed.

TABLE 10

| $NiCl_2$ (mM) | Relative activity (%) |
| --- | --- |
| 0 | 100 |
| 0.5 | 171 |
| 1.0 | 197 |
| 2.0 | 196 |
| 4.0 | 195 |
| 6.0 | 184 |
| 8.0 | 185 |

The enzyme incubated with nickel ion at 20° C. for five minutes, and the enzymatic activity was assayed.

16. The Effect of Coexisting $Ni^{++}$ Ion

As shown in Table 10, the enzymatic activity of nitrile hydratase of the present invention was enhanced twice by adding $Ni^{++}$ ion to the reaction system at a concentration of 1.0 mM. Then, with the standard composition of reaction solution shown in table 2, various types of substrates, instead of 3-cyanopyridine, were added to the solutions containing 2.92 U enzyme to study their effects on the activity. The activity was enhanced twice only when HMBN or mandelonitrile was used as the substrate. The addition of $Ni^{++}$ ion was assumed to specifically enhance the reaction efficiency when the substrate was a α-hydroxynitrile (Table 11).

TABLE 11

| Substrate | Free | $NiCl_2$ (1 mM) |
|---|---|---|
| HMBN | 100 | 196 |
| 3-cyanopyridine | 100 | 99 |
| 2-cyanopyridine | 100 | 97 |
| 4-cyanopyridine | 100 | 99 |
| n-butylonitrile | 100 | 94 |
| Chlotononitilile | 100 | 103 |
| Manderonitlile | 100 | 201 |
| Etylene cyanohydrin | 100 | 91 |
| Aminoacetonitlile | 0 | 0 |
| Hydroxyacetonitlile | 0 | 0 |
| 3-aminopropyonitrile | 100 | 97 |
| β-aminochlotononitlile | 0 | 0 |

The incubation was prolonged for 10 minutes at 20° C. using 2.92 U enzyme.

17. Determination of N-Terminal Amino Acid Sequence

The N-terminal amino acid sequences of α-subunit and β-subunit of nitrile hydratase from *Rhodococcus* sp. Cr4 strain were analyzed in a Procise Sequencer Model 470A from Applied Biosystem. The sequence of N-terminal 15 residues of α-subunit was TAHNPVQGTFPRSNE (SEQ ID NO: 5); that of β-subunit was MDGIHDLGGRAGLGP (SEQ ID NO: 6).

The respective sequences exhibited 93% identity to the sequence of N-terminal 15 residues of α-subunit and 100% identity to that of α-subunit of the low molecular weight nitrile hydratase from *Rhodococcus rhodochrous* J1 strain (Table 12/α-subunit; Table 13/β-subunit).

TABLE 12

| Strain | N-terminal amino acid sequence | Identity (%) |
|---|---|---|
| *Rhodococcus* sp. Cr4 | 1 TAHNPVQGTFPRSNE 15 | — |
| *Rhodococcus rhodochrous* J1 (low) | 1 TAHNPVQGTLPRSNE 15 | 93 |
| *Bacillus subtilis* | 211 VVSNPLAGSRPRSND 225 | 47 |

TABLE 13

| Strain | N-terminal amino acid sequence | Identity (%) |
|---|---|---|
| *Rhodococcus* sp. Cr4 | 1 MDGIHDLGGRAGLGP 15 | — |
| *Rhodococcus rhodochrous* J1 (low) | 1 MDGIHDLGGRAGLGP 15 | 100 |
| *Rhodococcus rhodochrous* J1 (high) | 1 MDGIHDTGGMTGYGP 15 | 73 |
| *Pseudomonas putida* | 1 MNGIHDTGGAHGYGP 15 | 67 |
| *Pseudomonas chlororaphis* B23 | 1 MDGFHDLGGFQGFGK 15 | 67 |

19. The Effect of Coexisting $NiCl_2$ and $CoCl_2$ in Resting Cell Reaction

The preculture medium of the following composition was aliquoted in 5 ml into each test tube (25×200 mm); a silicone plug was placed in the tube, followed by sterilization by autoclaving.

| Pre-culture medium (pH 7.0): | |
|---|---|
| Polypeptone | 5.0 g |
| Meat extract | 5.0 g |
| NaCl | 2.0 g |
| Yeast extract | 0.5 g |
| Distilled water | 1.0 L |

After the tube was cooled, *Rhodococcus* sp. Cr4 or *Rhodococcus rhodochrous* ATCC 332878 strain was inoculated with a platinum loop into the pre-culture medium, and then cultured with shaking at 28° C. for two days. Then, the pre-culture of *Rhodococcus* sp. Cr4 was transferred into main-culture medium 1; that of *Rhodococcus rhodochrous* ATCC 332878 was transferred into main-culture medium 2. Both were cultured with shaking at 33° C. for two days. The bacterial cells were harvested and washed, and then the reaction shown in Table 14 was carried out to study the effect of $NiCl_2$ and $CoCl_2$ added.

When $NiCl_2$ or $CoCl_2$ was added to the reaction system at a final concentration of 1 mM, as seen Table 15, the coexisting $NiCl_2$ or $CoCl_2$ enhanced the nitrile hydratase activity, and thus the addition of the ions had positive effect.

Main-Culture Medium 1 (for *Rhodococcus* sp. Cr4) (pH 7.0):

| Acetamide | 7.5 g |
|---|---|
| Glucose | 10.0 g |
| C.S.L. | 10.0 g |
| Yeast extract | 1.0 g |
| $MgSO_4 7H_2O$ | 0.5 g |
| $K_2HPO_4$ | 1.0 g |
| $CoCl_2 6H_2O$ | 10.0 mg |
| $FeSO_4 7H_2O$ | 10.0 mg |
| Distilled water | 1.0 L |

Main-Culture Medium 2 (for *Rhodococcus rhodochrous* ATCC 332878) (pH 7.0):

| ε-caprolactam | 5.0 g |
|---|---|
| Glucose | 10.0 g |
| C.S.L. | 10.0 g |
| Yeast extract | 1.0 g |
| $MgSO_4 7H_2O$ | 0.5 g |
| $K_2HPO_4$ | 1.0 g |
| $CoCl_2 6H_2O$ | 20.0 mg |
| Distilled water | 1.0 L |

Each medium was aliquoted in 20 ml into 500-ml Sakaguchi flasks, and then used after sterilized by autoclaving.

TABLE 14

| 10% (v/v) HMBN in 0.1 M KPB (pH 6.5) | 0.36 ml |
|---|---|
| 0.1 M KPB (pH 6.5) | 0.64 ml |
| Cell suspended solution (final: 0.05 fold) | 0.10 ml |

TABLE 14-continued

| | |
|---|---|
| 0.85% (w/v) NaClaq | 0.90, 0.80 ml |
| 20 mM NiCl$_2$ or CoCl$_2$ | 0.00, 0.10 ml |
| Total volume | 2.00 ml |

HMBN was added (reaction started).

The mixture was incubated with shaking at 20° C. for 15 minutes.

0.1%(v/v) H$_3$PO$_4$ was added (the reaction stopped).

Centrifugation.

HPLC analysis.

TABLE 15

| | Relative activity (%) | |
|---|---|---|
| | Rhodococcus sp. Cr4 | ATCC 332878 |
| Free | 100* | 100** |
| NiCl$_2$ | 186 | 193 |
| CoCl$_2$ | 137 | 123 |

*118 μmol/ml/min
**30.5 μmol/ml/min

In resting cell reaction, the enzymatic activity was also enhanced by NiCl$_2$ or CoCl$_2$ added.

20. The Effect of Cyanide Ion

The effect of cyanide ion on the nitrile hydratase of the present invention derived form Rhodococcus sp. Cr4, and known nitrile hydratase derived from Rhodococcus rhodochrous J1 (Biochimica et Biophysica Acta. 1129 (1991): 23-33) was studied. With the following standard composition of reaction solution, 0 mM-20 mM cyanide ion (KCN) was added to the reaction system. After the reaction solution was incubated in the absence of substrate (3-cyanopyridine) at 20° C. for 30 minutes, the substrate was added thereto to start the enzyme reaction. After the enzyme reaction at 20° C. for 10 minutes, 0.1 ml of 2 N hydrochloric acid was added thereto and the mixture was shaken vigorously to stop the reaction. The reaction solution was analyzed by HPLC by the same method as described in Section 1.

Standard Reaction Solution:

| | |
|---|---|
| 0.5 M 3-cyanopyridine | 0.5 ml |
| 0.1 M phosphate buffer (pH 7.5) | 0.25 ml |
| Enzyme solution | 0.1 ml |
| Total volume | 1.0 ml |

In the case of Rhodococcus sp. Cr4 nitrile hydratase, the quantity of enzyme used was 288 U/ml; in the case of Rhodococcus rhodochrous J1 nitrile hydratase, the quantity of enzyme used was 61 U/ml. As seen in Table 16, the nitrile hydratase of Rhodococcus rhodochrous J1 was completely inhibited in the presence of 1 mM cyanide ion, but the nitrile hydratase of Rhodococcus sp. Cr4 retained 47% of the activity in the presence of 1 mM cyanide ion and 17% of the activity in the presence of 5 mM cyanide ion.

TABLE 16

| KCN (mM) | Cr4 | J1 |
|---|---|---|
| 0 | 100% | 100% |
| 1 | 47 | 0 |
| 5 | 17 | 0 |
| 10 | 11 | 0 |
| 15 | 8 | 0 |
| 20 | 3 | 0 |

21. Determination of N-Terminal Amino Acid Sequence

The nitrile hydratase purified from Rhodococcus sp. Cr4 was subjected to SDS-PAGE. The protein was electrotransferred onto a PVDF membrane with a Horiz-Blot Electrophoresis Apparatus Model AE6678-P (ATTO), and then stained with amide black. Portions corresponding to α-subunit and β-subunit were cut off, and each of the subunit proteins were subjected to automatic Edman degradation in a gas-phase peptide sequencer model 473A (Applied Biosystem), and thus PTH amino acid derivatives were obtained. The N-terminal amino acid sequences of α-subunit and β-subunit were analyzed in a PTH amino acid derivative analyzer model 120A (Applied Biosystem).

The N-terminal sequence was TAHNPVQGTFPRSNE (SEQ ID NO: 5) for α-subunit; MDGIHDLGGRAGLGPI (SEQ ID NO: 7) for β-subunit. The sequence of α-subunit exhibited 93% identity (L at amino acid residue 10 in J1) to the N-terminal sequence of α-subunit of low-molecularweight nitrile hydratase from Rhodococcus rhodochrous J1; the sequence of β-subunit did 100% identity to that of the equivalent from Rhodococcus rhodochrous J1.

Thus, the N-terminal amino acid sequences of nitrile hydratase α-subunit and β-subunit from Rhodococcus rhodochrous J1 are nearly identical to those from Rhodococcus sp. Cr4. Further, it is known that α-subunits of previously reported nitrile hydratases share the highly homologous primary structures. Thus, cloning of the nitrile hydratase gene of Rhodococcus sp. Cr4 was carried out using, as a probe DNA, a gene fragment from α-subunit of nitrile hydratase of Rhodococcus rhodochrous J1. Further, a gene fragment form β-subunit of nitrile hydratase of Rhodococcus rhodochrous J1 was used to evaluate whether the entire region of nitrile hydratase gene of Rhodococcus sp. Cr4 was successfully cloned.

22. Preparation of Probe DNA

There two types of nitrile hydratases in Rhodococcus rhodochrous J1, namely, the low molecular weight form and high molecular weight form. Therefore, firstly, regions of the primary structure of low molecular weight nitrile hydratase gene, of which sequences are different from those corresponding regions of the high molecular weight form, in Rhodococcus rhodochrous J1, were selected. Specifically, the respective amino acid sequences selected are described below.

α-Subunit:
Sense primer region: QGTLPRSN (SEQ ID NO: 8)
Antisense primer region: PDPDVEIR (SEQ ID NO: 9)

β-Subunit:
Sense primer region:. PHDYLTSQ (SEQ ID NO: 10)
Antisense primer region: PNVVNHID (SEQ ID NO: 11)

Then, based on the amino acid sequences, PCR primers, to be used for specifically amplifying a part of the low molecular weight nitrile hydratase gene, were actually designed. Finally, the primers comprising the following nucleotide sequences were designed.

α-Subunit Gene Fragment for Amplification:
sense primer: 5'-cagggcacgttgccacgatcg-3' (SEQ ID NO: 12)
antisense primer: 5'-cggatctcgacgtcagggtcg-3' (SEQ ID NO: 13)

β-Subunit Gene Fragment for Amplification:
sense primer: 5'-cgcacgactacctgacctcgc-3' (SEQ ID NO: 14)
antisense primer: 5'-cgatgtgattgactacgttcgg-3' (SEQ ID NO: 15)

Then, the genomic DNA was prepared from *Rhodococcus rhodochrous* J1 according to the method of Ausbel et al. (Ausbel, F M et al: UNIT 2.4, Preparation of Genomic DNA from Bacteria in Current Protocols in Molecular Biology (John Wiley and Sons, New York) 1987). Further, the genomic DNA was also prepared from culture cells of *Rhodococcus* sp. Cr4 by the same method.

A part of the low molecular weight nitrile hydratase gene of *Rhodococcus rhodochrous* J1 was amplified by PCR using Taq DNA 30 (Takara Shuzo) and cycles of: denaturation at 94° C. for 1 minutes, annealing at 60° C. for 90 seconds, and extension at 72° C. for 90 seconds using 10 ng of the genomic DNA obtained as a template. Amplified DNA fragment was subjected to agarose gel electrophoresis and then collected from the gel by using a RECOCHIP (Takara Shuzo).

PCR amplification using the primers for the amplification of α-subunit gene fragment and the genomic DNAs from *Rhodococcus rhodochrous* J1 and *Rhodococcus* sp. Cr4 as templates gave amplification products of about 450 bp from both strains. However, when the genomic DNA from *Rhodococcus* sp. Cr4 was used as the template, the efficiency of PCR amplification was lower. Thus, the amplified fragment by using the genomic DNA of *Rhodococcus rhodochrous* J1 as the template was used as the probe DNA for the subsequent experiments.

The amplified DNA fragment derived from *Rhodococcus rhodochrous* J1 was labeled with digoxigenin according to the random priming method with a DIG-labeling kit (Boehringer Manheim). The digoxigenin-labeled DNA fragment was used as the probe DNA in the subsequent Southern blot analysis and colony hybridization.

23. Southern Blot Analysis

The genomic DNA of *Rhodococcus* sp. Cr4 was digested with various restriction enzymes, and analyzed by Southern blotting using the probe DNA from α-subunit of nitrile hydratase derived from *Rhodococcus rhodochrous* J1. 10 μg of the genomic DNA from *Rhodococcus* sp. Cr4 was completely digested with PstI, SphI and BanIII (Toyobo), and then 1-μg aliquots of the digests were electrophoresed on a 0.8% agarose gel. The DNA was transferred onto a nylon membrane NY13N (Schleicher & Schuel) in a vacuum blotter model 785 (Bio-Rad) according to the attached manual. The DNA was immobilized on the membrane in an autocrosslinker CL-1000 (BM Equipment) The resulting membrane was hybridized with the probe DNA at 60° C. overnight, and then washed at room temperature for 5 minutes and then at 60° C. for 15 minutes. The chemical luminescent light by CDP-Star was exposed onto a Fuji RX film for signal detection by using a DIG detection kit (Boehringer Manheim) according to the attached manual.

The analysis of Southern blotting revealed single bands of 3.2 kb, 4.2 kb and 7.8 kb in the lanes of the genomic DNA from *Rhodococcus* sp. Cr4 digested with PstI, SphI and BanIII, respectively. The nitrile hydratase gene of *Rhodococcus* sp. Cr4 was found to be a single-copy gene. The nitrile hydratase gene of *Rhodococcus* sp. Cr4 was cloned from a genomic library prepared from the PstI digest.

24. Preparation of a Genomic Library of *Rhodococcus* sp. Cr4 and Colony Hybridization A plasmid pBluescript II SK (+) (Stratagene) was digested with PstI, and then dephosphorylated by bacterial alkaline phosphatase (Takara Shuzo). The genomic DNA of *Rhodococcus* sp. Cr4 was digested with PstI, and then ligated to the above pBluescript II SK (+) by using T4 DNA ligase (Takara Shuzo). Then, *E. coli* DH5α was transformed by above-mentioned vector.

Colony hybridization was performed according to the method of Sambrook et al. (Molecular cloning (Cold Spring Harbor Laboratory Press, Cold Spring Harbor) 1989). Specifically, a nitrocellulose filter was placed on an LB agar plate containing 50 μg/ml ampicillin, and the transformants obtained were spread thereon. The plate was incubated at 37° C. overnight. After the colonies were formed, a replica filter prepared was placed on the agar plate and cultured thereon. After the colonies were formed on the replica filter., the filter was transferred onto an agar plate containing 200 μg/ml chloramphenicol. The plate was incubated at 37° C. for 24 hours. The filter was treated with SDS and alkali to lyse the colonies. Then, colony hybridization was carried out under the same conditions as used in the analysis of Southern blotting. Thus, a positive clone was obtained from about 2000 colonies.

25. Analyses of the Positive Clone

After the positive clone was cultured, the plasmid was prepared by the alkali-SDS method; the plasmid was named pNHCr4P. The plasmid PNHCr4P contained an insert of about 3.2-kb DNA fragment.

In order to confirm that the insert DNA fragment of pNHCr4P contains the β-subunit gene, a probe DNA was prepared by PCR using the primers for the amplification of the β-subunit gene fragment and the genomic DNA of *Rhodococcus rhodochrous* J1 as a template. With this probe DNA, pNHCr4P was analyzed by Southern blotting. As a result, the insert fragment of about 3.2 kb containing the β-subunit gene was confirmed.

The nucleotide sequence of insert DNA fragment (about 3.2 kb) in pNHCr4P was analyzed by the dideoxy chain termination method using a DNA sequencer model 377A (Applied Biosystem) and Taq primer cycle sequencing kit (Applied Biosystem). The determined nucleotide sequence is shown in SEQ ID NO: 16. The sequencing result showed that the size of PstI insert DNA fragment in pNHCr4P was 3205 bp and that an ORF was presence (FIG. 12). The organization of gene cluster in *Rhodococcus* sp. Cr4 was very similar to the region containing the low molecular weight nitrile hydratase gene in *Rhodococcus rhodochrous* J1 (Komeda et al: Proc Natl Acad Sci USA 94: 36-41, 1997).

26. Analysis of Primary Structure

The primary structures of α-subunit and β-subunit deduced from the region of nucleotides 245-2100 of the PstI fragment are shown in SEQ ID NO: 2 and SEQ ID NO: 4, respectively. The N-terminal amino acid sequences of α-subunit and β-subunit completely agreed with those determined with the protein sequencer. In addition, both α-subunit and β-subunit exhibited the most-homologies to those of nitrile hydratase from *Rhodococcus rhodochrous* J1 (Table 17).

TABLE 17

|  | α | β |
|---|---|---|
| R. rhodochrous J1 (low molecule type) | 92% | 87% |
| Rhodococcus sp. | 65% | 45% |
| Pseudomonas putida | 59% | 37% |
| Bacillus sp. BR449 | 60% | 38% |
| Mesorhizobium loti | 56% | 38% |
| Sinorhizobium meliloti | 55% | 39% |
| Rhodococcus sp. M8 | 52% | 37% |
| R. rhodochrous J1 (high molecule type) | 52% | 37% |
| R. erythropolis | 50% | 35% |
| Pseudomonas chlororaphis B23 | 50% | 31% |
| Brevibacterium sp. R312 | 50% | ? |
| Patent No. W09504828 | 42% | 34% |

17 amino acid residues of 207 residues of α-subunits of nitrile hydratase were different between *Rhodococcus* sp. Cr4 (SEQ ID NO: 2) and *Rhodococcus rhodochrous* J1 (SEQ ID NO: 18). Further, 29 amino acid residues of 227 residues of β-subunit of nitrile hydratase were different between *Rhodococcus* sp. Cr4 (SEQ ID NO: 4) and *Rhodococcus rhodochrous* J1 (SEQ ID NO: 19) (FIGS. 13 and 14).

INDUSTRIAL APPLICABILITY

The present invention provides a nitrile hydratase capable of producing 2-hydroxy-4-methylthiobutyroamide from 2-hydroxy-4-methylthiobutyronitrile as a substrate. 2-hydroxy-4-methylthiobutyroamide is a useful compound as a feed additive (a methionine substitute).

Not only the present invention provides the nitrile hydratase capable of enzymatically producing 2-hydroxy-4-methylthiobutyroamide, but also the encoding gene was cloned in the present invention. The nitrile hydratase of the present invention can be expressed at high levels in appropriate host cells transformed with the gene encoding the nitrile hydratase provided by the present invention. Thus, the transformants themselves that can be obtained according to the present invention, or the enzyme protein obtained from the transformants, are useful for enzymatically producing 2-hydroxy-4-methylthiobutyroamide. Though many of known nitrile hydratases produced by genetic recombination could not achieve high enzymatic activity, the nitrile hydratase of the present invention is excellent retaining the high activity even when it is a genetic recombinant.

Further, the nitrile hydratase of the present invention retains the high enzymatic activity in the presence of cyanide or aldehyde. In a polar solvent, α-hydroxynitrile as the substrate compound is decomposed to hydrocyanic acid and aldehyde. Hydrocyanic acid is converted to cyanide, which often reduces the enzymatic activity. Aldehyde also gives damages to the protein and reduces the enzymatic activity. One of the reasons why known nitrile hydratases were not industrially applicable was that these cyanide and aldehyde reduces the enzymatic activity.

The hydratase of the present invention retains the enzymatic activity even in the presence of cyanide or aldehyde. Therefore, α-hydroxynitrile produced from aldehyde and hydrocyanic acid can be used as the substrate. Thus, the nitrile hydratase of the present invention is useful for the method for producing amides using α-hydroxynitrile as starting material.

The invention claimed is:

1. An isolated protein complex consisting of an α-subunit protein and a β-subunit protein, wherein said protein complex is capable of converting:
a nitrile group of a nitrile compound to an amide group; and
wherein the α subunit protein is a protein selected from the group consisting of:

(A) a protein comprising the amino acid sequence of SEQ ID NO: 2;

(B) a protein comprising the amino acid sequence of SEQ ID NO: 2 in which one to ten amino acids are substituted, deleted, inserted and/or added;

(C) a protein having 95% or higher identity to the amino acid sequence of SEQ ID NO: 2;

(D) a protein encoded by a polynucleotide comprising the nucleotide sequence of SEQ ID NO:1; and (E) a protein encoded by a polynucleotide that hybridizes to the nucleotide sequence of SEQ ID NO:1 under stringent conditions of 6×SSC at about 45° C., followed by one or more washes in 0.2×SSC, 0.1% SDS at 65° C.;

and wherein the β subunit protein is a protein selected from the group consisting of:

(a) a protein comprising the amino acid sequence of SEQ ID NO: 4;

(b) a protein comprising the amino acid sequence of SEQ ID NO: 4 in which one to ten amino acids are substituted, deleted, inserted and/or added;

(c) a protein having 95% or higher identity to the amino acid sequence of SEQ ID NO: 4;

(d) a protein encoded by a polynucleotide comprising the nucleotide sequence of SEQ ID NO:3; and (e) a protein encoded by a polynucleotide that hybridizes to the nucleotide sequence of SEQ ID NO:3 under stringent conditions of 6×SSC at about 45° C., followed by one or washes in 0.2×SSC, 0.1% SDS at 65° C.

2. The protein complex according to claim 1, wherein the α-subunit protein comprises the amino acid sequence of SEQ ID NO: 2.

3. The protein complex according to claim 1, wherein the β-subunit protein comprises the amino acid sequence of SEQ ID NO: 4.

4. An isolated protein selected from the group consisting of:

(A) an α-subunit protein comprising the amino acid sequence of SEQ ID NO: 2;

(B) an α-subunit protein comprising the amino acid sequence of SEQ ID NO: 2 in which one to ten amino acids are substituted, deleted, inserted and/or added, wherein said α-subunit protein is capable of forming a protein complex with any β-subunit protein defined below in subsections (F) to (J) and said protein complex is capable of converting a nitrile group of a nitrile compound to an amide group;

(C) an α-subunit protein having 95% or higher identity to the amino acid sequence of SEQ ID NO: 2, wherein said α-subunit protein is capable of forming a protein complex with any β-subunit protein defined below in subsections (F) to (J) and said protein complex is capable of converting a nitrile group of a nitrile compound to an amide group;

(D) an α-subunit protein encoded by a polynucleotide comprising the nucleotide sequence of SEQ ID NO:1;

(E) an α-subunit protein encoded by a polynucleotide that hybridizes to the nucleotide sequence of SEQ ID NO:1 under stringent conditions of 6×SSC at about 45° C., followed by one or more washes in 0.2×SSC, 0.1% SDS at 65° C., wherein said α-subunit protein is capable of forming a protein complex with any β-subunit protein defined below in subsections (F) to (J) and said protein complex is capable of converting a nitrile group of a nitrile compound to an amide group;

(F) a β-subunit protein comprising the amino acid sequence of SEQ ID NO: 4;

(G) a β-subunit protein comprising the amino acid sequence of SEQ ID NO: 4 in which one to ten amino acids are substituted, deleted, inserted and/or added, wherein said β-subunit protein is capable of forming a protein complex with any α-subunit protein defined above in subsections (A) to (E) and said protein complex is capable of converting a nitrile group of a nitrile compound to an amide group;

(H) a β-subunit protein having 95% or higher identity to the amino acid sequence of SEQ ID NO: 4, wherein said β-subunit is capable of forming a protein complex with any α-subunit protein defined above in subsections (A) to (E) and said protein complex is capable of converting a nitrile group of a nitrile compound to an amide group;

(I) a β-subunit protein encoded by a polynucleotide comprising the nucleotide sequence of SEQ ID NO:3; and (J) a β-subunit protein encoded by a polynucleotide that hybridizes to the nucleotide sequence of SEQ ID NO:3 under stringent conditions of 6×SSC at about 45° C., followed by one or more washes in 0.2×SSC, 0.1% SDS at 65° C., wherein said β-subunit protein is capable of forming a protein complex with any α-subunit protein defined above in subsections (A) to (E) and said protein complex is capable of converting a nitrile group of a nitrile compound to an amide group.

5. The protein complex according to claim 1, wherein the α-subunit protein comprises the amino acid sequence of SEQ ID NO:2 and the β-subunit protein comprises the amino acid sequence of SEQ ID NO:4.

6. The protein complex according to claim 1, wherein the protein complex is derived from *Rhodococcus sp.* Cr4 strain that has been deposited under the accession numbed FERM BP-6596.

7. The protein complex according to claim 1, wherein the protein complex is capable of converting 2-hydroxy-4-methylthiobutyronitrile to 2-hydroxy-4-methylthiobutyroamide.

* * * * *

UNITED STATES PATENT AND TRADEMARK OFFICE
CERTIFICATE OF CORRECTION

| | | |
|---|---|---|
| PATENT NO. | : 7,300,784 B2 | Page 1 of 1 |
| APPLICATION NO. | : 10/469427 | |
| DATED | : November 27, 2007 | |
| INVENTOR(S) | : Toru Nagasawa | |

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by (379) days Delete the phrase "by 379 days" and insert -- by 433 days --

Signed and Sealed this

Twenty-seventh Day of January, 2009

JOHN DOLL
*Acting Director of the United States Patent and Trademark Office*

SEQUENCE LISTING

```
<160> NUMBER OF SEQ ID NOS: 18

<210> SEQ ID NO 1
<211> LENGTH: 681
<212> TYPE: DNA
<213> ORGANISM: Rhodococcus sp.
<220> FEATURE:
<221> NAME/KEY: CDS
<222> LOCATION: (1)..(681)

<400> SEQUENCE: 1 atg gat ggt atc cac gat ctg ggc ggg cgc gcc ggt ctg ggg ccg gtc      48
Met Asp Gly Ile His Asp Leu Gly Gly Arg Ala Gly Leu Gly Pro Val
 1               5                  10                  15 aat ccc gaa ccc ggt gag ccg gtc ttt cat tct cgt tgg gag cgg tcg      96
Asn Pro Glu Pro Gly Glu Pro Val Phe His Ser Arg Trp Glu Arg Ser
            20                  25                  30 gtt ttg acg atg ttt ccg gcc atg gcg tta gcc ggg gcg ttc aac ctc     144
Val Leu Thr Met Phe Pro Ala Met Ala Leu Ala Gly Ala Phe Asn Leu
        35                  40                  45 gac cag ttc cgg ggc gcg atg gaa cag att ccc ccg cac gac tat ctg     192
Asp Gln Phe Arg Gly Ala Met Glu Gln Ile Pro Pro His Asp Tyr Leu
    50                  55                  60 acc tcg cag tac tac gag cac tgg atg cac gcg atg atc cac tac ggc     240
Thr Ser Gln Tyr Tyr Glu His Trp Met His Ala Met Ile His Tyr Gly
65                  70                  75                  80 atc gag gcg ggc atc ttc gac ccg aac gag ctc gac cgt cgc acc cag     288
Ile Glu Ala Gly Ile Phe Asp Pro Asn Glu Leu Asp Arg Arg Thr Gln
                85                  90                  95
```

| | | |
|---|---|---|
| tac tac ctg gag cat ccg gac gaa gac ccg ccc ctg cgg cag gac ccg<br>Tyr Tyr Leu Glu His Pro Asp Glu Asp Pro Pro Leu Arg Gln Asp Pro<br>               100                        105               110 | 336 |
| cag ttg gtg gag acg atc tcg cag ttg atc atg cac gga gcc gac tac<br>Gln Leu Val Glu Thr Ile Ser Gln Leu Ile Met His Gly Ala Asp Tyr<br>      115                     120                    125 | 384 |
| cga agg ccg acc gac gcc gag ggc gtc ttc gcg gtg ggc gac aag gtc<br>Arg Arg Pro Thr Asp Ala Glu Gly Val Phe Ala Val Gly Asp Lys Val<br>130                        135                    140 | 432 |
| gtt gtg cgg tcg gac gcc tcg ccg aac acc cac acc cgt cgc gcc ggc<br>Val Val Arg Ser Asp Ala Ser Pro Asn Thr His Thr Arg Arg Ala Gly<br>145                      150                     155                   160 | 480 |
| tac atc cgt gga cgc acc ggt gag atc gtc gca gct cac ggc gcc tac<br>Tyr Ile Arg Gly Arg Thr Gly Glu Ile Val Ala Ala His Gly Ala Tyr<br>                     165                    170                 175 | 528 |
| gtt ttc ccg gac act aac gcc gtc ggc gcc ggc gaa cac ccc gaa cac<br>Val Phe Pro Asp Thr Asn Ala Val Gly Ala Gly Glu His Pro Glu His<br>                180                     185                   190 | 576 |
| ctg tac acg gtg cgg ttc tcg gcg acc gag ttg tgg ggc gag acc gcc<br>Leu Tyr Thr Val Arg Phe Ser Ala Thr Glu Leu Trp Gly Glu Thr Ala<br>      195                     200                    205 | 624 |
| acc tcc aac gcg gtc aac cac atc gac gtg ttc gaa ccc tac ctg ctg<br>Thr Ser Asn Ala Val Asn His Ile Asp Val Phe Glu Pro Tyr Leu Leu<br>210                        215                     220 | 672 |
| ccg gcc tga<br>Pro Ala<br>225 | 681 |

<210> SEQ ID NO 2
<211> LENGTH: 226
<212> TYPE: PRT
<213> ORGANISM: Rhodococcus sp.

<400> SEQUENCE: 2

Met Asp Gly Ile His Asp Leu Gly Gly Arg Ala Gly Leu Gly Pro Val
1               5                     10                   15

Asn Pro Glu Pro Gly Glu Pro Val Phe His Ser Arg Trp Glu Arg Ser
                   20                     25                   30

Val Leu Thr Met Phe Pro Ala Met Ala Leu Ala Gly Ala Phe Asn Leu
               35                     40                   45

Asp Gln Phe Arg Gly Ala Met Glu Gln Ile Pro Pro His Asp Tyr Leu
          50                     55                   60

Thr Ser Gln Tyr Tyr Glu His Trp Met His Ala Met Ile His Tyr Gly
65                 70                     75                   80

Ile Glu Ala Gly Ile Phe Asp Pro Asn Glu Leu Asp Arg Arg Thr Gln
               85                     90                   95

Tyr Tyr Leu Glu His Pro Asp Glu Asp Pro Pro Leu Arg Gln Asp Pro
               100                    105                   110

Gln Leu Val Glu Thr Ile Ser Gln Leu Ile Met His Gly Ala Asp Tyr
          115                     120                    125

Arg Arg Pro Thr Asp Ala Glu Gly Val Phe Ala Val Gly Asp Lys Val
130                        135                    140

Val Val Arg Ser Asp Ala Ser Pro Asn Thr His Thr Arg Arg Ala Gly
145                      150                     155                   160

Tyr Ile Arg Gly Arg Thr Gly Glu Ile Val Ala Ala His Gly Ala Tyr
               165                    170                   175

Val Phe Pro Asp Thr Asn Ala Val Gly Ala Gly Glu His Pro Glu His
          180                     185                    190

```
Leu Tyr Thr Val Arg Phe Ser Ala Thr Glu Leu Trp Gly Glu Thr Ala
            195                 200                 205

Thr Ser Asn Ala Val Asn His Ile Asp Val Phe Glu Pro Tyr Leu Leu
        210                 215                 220

Pro Ala
225

<210> SEQ ID NO 3
<211> LENGTH: 624
<212> TYPE: DNA
<213> ORGANISM: Rhodococcus sp.
<220> FEATURE:
<221> NAME/KEY: CDS
<222> LOCATION: (1)..(624)

<400> SEQUENCE: 3 atg acc gcc cac aat ccc gtc cag ggc acc ttc ccc cga tcg aac gag        48
Met Thr Ala His Asn Pro Val Gln Gly Thr Phe Pro Arg Ser Asn Glu
  1               5                  10                  15 gag atc gcc gcc cgc gtc aag gcc atg gag gcc atc ctc gtc gac aag        96
Glu Ile Ala Ala Arg Val Lys Ala Met Glu Ala Ile Leu Val Asp Lys
                 20                  25                  30 ggc ctg atc tcc acc gac gcc atc gac tac atg tcc tcg gtc tac gag       144
Gly Leu Ile Ser Thr Asp Ala Ile Asp Tyr Met Ser Ser Val Tyr Glu
             35                  40                  45 aac gag gtc ggt cct cag ctc ggc gcc aag atc gcc gcc cat gcc tgg       192
Asn Glu Val Gly Pro Gln Leu Gly Ala Lys Ile Ala Ala His Ala Trp
         50                  55                  60 gtc gat ccc gag ttc aaa cag cgc ctc ctc gcc gac gca acc ggc gcc       240
Val Asp Pro Glu Phe Lys Gln Arg Leu Leu Ala Asp Ala Thr Gly Ala
 65                  70                  75                  80 tgc aag gaa atg ggc gtc ggc ggg atg cag ggc gaa gaa atg gtc gtg       288
Cys Lys Glu Met Gly Val Gly Gly Met Gln Gly Glu Glu Met Val Val
                 85                  90                  95 ctg gaa aac acc gac acc gtc aac aac atg gtc gtg tgc acc ctg tgc       336
Leu Glu Asn Thr Asp Thr Val Asn Asn Met Val Val Cys Thr Leu Cys
            100                 105                 110 tcg tgc tac ccg tgg ccg gtg ctc gga ttg ccg ccc aac tgg tac aag       384
Ser Cys Tyr Pro Trp Pro Val Leu Gly Leu Pro Pro Asn Trp Tyr Lys
        115                 120                 125 tac ccc gcc tac cgc gcc cgc gcc gcc cgc gac ccg cga ggg gtg atg       432
Tyr Pro Ala Tyr Arg Ala Arg Ala Ala Arg Asp Pro Arg Gly Val Met
    130                 135                 140 gcc gag ttc ggc tat acc ccc gcc tcg gac gtc gag atc cgg gtg tgg       480
Ala Glu Phe Gly Tyr Thr Pro Ala Ser Asp Val Glu Ile Arg Val Trp
145                 150                 155                 160 gac tcg agc gcc gaa ctg cgc tac tgg gtg ctg ccg cag cgc ccc gcc       528
Asp Ser Ser Ala Glu Leu Arg Tyr Trp Val Leu Pro Gln Arg Pro Ala
                165                 170                 175 ggc acc gag aac ttc acc gaa gag cag ctc gcc gcc ctc gtc acc cgc       576
Gly Thr Glu Asn Phe Thr Glu Glu Gln Leu Ala Ala Leu Val Thr Arg
            180                 185                 190 gac tcg ctc atc ggc gtg tcc gtc ccc acc gca ccg aac aag gcc tga       624
Asp Ser Leu Ile Gly Val Ser Val Pro Thr Ala Pro Asn Lys Ala
        195                 200                 205

<210> SEQ ID NO 4
<211> LENGTH: 207
<212> TYPE: PRT
<213> ORGANISM: Rhodococcus sp.
```

-continued

```
<400> SEQUENCE: 4

Met Thr Ala His Asn Pro Val Gln Gly Thr Phe Pro Arg Ser Asn Glu
  1               5                  10                  15

Glu Ile Ala Ala Arg Val Lys Ala Met Glu Ala Ile Leu Val Asp Lys
                 20                  25                  30

Gly Leu Ile Ser Thr Asp Ala Ile Asp Tyr Met Ser Ser Val Tyr Glu
             35                  40                  45

Asn Glu Val Gly Pro Gln Leu Gly Ala Lys Ile Ala Ala His Ala Trp
 50                  55                  60

Val Asp Pro Glu Phe Lys Gln Arg Leu Leu Ala Asp Ala Thr Gly Ala
 65                  70                  75                  80

Cys Lys Glu Met Gly Val Gly Gly Met Gln Gly Glu Glu Met Val Val
                 85                  90                  95

Leu Glu Asn Thr Asp Thr Val Asn Asn Met Val Val Cys Thr Leu Cys
            100                 105                 110

Ser Cys Tyr Pro Trp Pro Val Leu Gly Leu Pro Pro Asn Trp Tyr Lys
            115                 120                 125

Tyr Pro Ala Tyr Arg Ala Arg Ala Ala Arg Asp Pro Arg Gly Val Met
130                 135                 140

Ala Glu Phe Gly Tyr Thr Pro Ala Ser Asp Val Glu Ile Arg Val Trp
145                 150                 155                 160

Asp Ser Ser Ala Glu Leu Arg Tyr Trp Val Leu Pro Gln Arg Pro Ala
                165                 170                 175

Gly Thr Glu Asn Phe Thr Glu Gln Leu Ala Ala Leu Val Thr Arg
            180                 185                 190

Asp Ser Leu Ile Gly Val Ser Val Pro Thr Ala Pro Asn Lys Ala
            195                 200                 205

<210> SEQ ID NO 5
<211> LENGTH: 15
<212> TYPE: PRT
<213> ORGANISM: Rhodococcus sp.

<400> SEQUENCE: 5

Thr Ala His Asn Pro Val Gln Gly Thr Phe Pro Arg Ser Asn Glu
  1               5                  10                  15

<210> SEQ ID NO 6
<211> LENGTH: 15
<212> TYPE: PRT
<213> ORGANISM: Rhodococcus sp.

<400> SEQUENCE: 6

Met Asp Gly Ile His Asp Leu Gly Gly Arg Ala Gly Leu Gly Pro
  1               5                  10                  15

<210> SEQ ID NO 7
<211> LENGTH: 16
<212> TYPE: PRT
<213> ORGANISM: Rhodococcus sp.

<400> SEQUENCE: 7

Met Asp Gly Ile His Asp Leu Gly Gly Arg Ala Gly Leu Gly Pro Ile
  1               5                  10                  15

<210> SEQ ID NO 8
<211> LENGTH: 8
<212> TYPE: PRT
<213> ORGANISM: Rhodococcus sp.
```

-continued

```
<400> SEQUENCE: 8

Gln Gly Thr Leu Pro Arg Ser Asn
  1               5

<210> SEQ ID NO 9
<211> LENGTH: 8
<212> TYPE: PRT
<213> ORGANISM: Rhodococcus sp.

<400> SEQUENCE: 9

Pro Asp Pro Asp Val Glu Ile Arg
  1               5

<210> SEQ ID NO 10
<211> LENGTH: 8
<212> TYPE: PRT
<213> ORGANISM: Rhodococcus sp.

<400> SEQUENCE: 10

Pro His Asp Tyr Leu Thr Ser Gln
  1               5

<210> SEQ ID NO 11
<211> LENGTH: 8
<212> TYPE: PRT
<213> ORGANISM: Rhodococcus sp.

<400> SEQUENCE: 11

Pro Asn Val Val Asn His Ile Asp
  1               5

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 12
cagggcacgt tgccacgatc g                                            21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 13
cggatctcga cgtcagggtc g                                            21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 14
cggatctcga cgtcagggtc g                                            21
```

-continued

```
<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 15
cgatgtgatt gactacgttc gg                                              22

<210> SEQ ID NO 16
<211> LENGTH: 3205
<212> TYPE: DNA
<213> ORGANISM: Rhodococcus sp.

<400> SEQUENCE: 16
ctgcagtgtg cgcggcccgg gacgagcgac ggggtctcga ggactcgtcc accatgctcg      60
ccgatccggg gggcagacga aaagacaatg agttgagtga atgaggcgta actgaatcta     120
gactagtggg ggcctgtcgg gttgtccaga gcgtgtcgtc gcgcgcagga aagcgtcaaa     180
aatcaactgc cgcaacgttt gctccggaat gaggcagctc ccctgttgcg cccatgcggg     240
ggagtctgcc ctctggatcc cccgtgcgag aggcaacaaa atcttaacag gtcacgaagt     300
catgacctat tgacctatcg ggattgtggt gtttaaggtt ggtgacccaa gccacaagga     360
ggcaatgcga tggatggtat ccacgatctg ggcgggcgcg ccggtctggg gccggtcaat     420
cccgaacccg gtgagccggt ctttcattct cgttgggagc ggtcggtttt gacgatgttt     480
ccggccatgg cgttagccgg ggcgttcaac ctcgaccagt tccggggcgc gatggaacag     540
attcccccgc acgactatct gacctcgcag tactacgagc actggatgca cgcgatgatc     600
cactacggca tcgaggcggg catcttcgac ccgaacgagc tcgaccgtcg cacccagtac     660
tacctggagc atccggacga agacccgccc ctgcggcagg acccgcagtt ggtggagacg     720
atctcgcagt tgatcatgca cggagccgac taccgaaggc cgaccgacgc cgagggcgtc     780
ttcgcggtgg gcgacaaggt cgttgtgcgc tcggacgcct cgccgaacac ccacacccgt     840
cgcgccggct acatccgtgg acgcaccggt gagatcgtcg cagctcacgg cgcctacgtt     900
ttcccggaca ctaacgccgt cggcgccggc gaacaccccg aacacctgta cacggtgcgg     960
ttctcggcga ccgagttgtg gggcgagacc gccacctcca acgcggtcaa ccacatcgac    1020
gtgttcgaac cctacctgct gccggcctga ccggagcgtc cgatacaacc tcgctgatac    1080
ccccactgcc ccgcctacgg aaacgagttc acccgatgac cgcccacaat cccgtccagg    1140
gcaccttccc ccgatcgaac gaggagatcg ccgcccgcgt caaggccatg gaggccatcc    1200
tcgtcgacaa gggcctgatc tccaccgacg ccatcgacta catgtcctcg gtctacgaga    1260
acgaggtcgg tcctcagctc ggcgccaaga tcgccgccca tgcctgggtc gatcccgagt    1320
tcaaacagcg cctgctcgcc gacgcaaccg cgcctgcaa ggaaatgggc gtcggcggga    1380
tgcagggcga agaaatggtc gtgctggaaa acaccgacac cgtcaacaac atggtcgtgt    1440
gcaccctgtg ctcgtgctac ccgtggccgg tgctcggatt gccgcccaac tggtacaagt    1500
accccgccta ccgcgcccgc gccgcccgcg accgcgagg ggtgatggcc gagttcggct    1560 ataccccgc ctcggacgtc gagatccggg tgtgggactc gagcgccgaa ctgcgctact    1620
gggtgctgcc gcagcgcccc gccggcaccg agaacttcac cgaagagcag ctcgccgccc    1680
tcgtcacccg cgactcgctc atcggcgtgt ccgtccccac cgcaccgaac aaggcctgac    1740
atgccccaac tcaacgaaca acccagccag gacctcaagg accgcctcga cggcctggtg    1800
```

```
cagaaccta cgttcaacga gcagattccc cggcgctccg gggaggtcgc cttcgaccat    1860
gcctgggaga tccgcgcttt cagcatcgcc accgccctgc atgcccaggg ccggttcgag    1920
tgggacgaat tccagtcccg cctgatcgac tcgatcaaac agtgggaaac cgaacacacc    1980
accaccgagg agtggagcta ctacgagtgt tggatgctcg cactcgaaga gctggtgcgg    2040 gacaagggc tggtcgccgg tgatgaactc gagcaccgca ccgagcaggt gctggccacc    2100
ccggccaacg cccaccacca acacgctgta cgcgacccca ttgccgtgca caccagcgaa    2160
gtacctactg ctcagtactc ccggtagccc ctggggcctc gccttcacgg aggtggaact    2220
ctcgtgtaaa ggctcctggg ctctgcgacg tagagatacc accgatcttt ctcttgggct    2280
ccccaggagc cgaagacgca tccctgatat ggcaactcgg acctggccgg gcgcgcagac    2340
acaacgtgcg agcgccccgg aacttccaag cctctggcgt attcggaaga cgctgcgaat    2400
tagtcgaagg acaagggttt gaccagtacc gcaatgacac cgcaccgcat gggcggtgcg    2460
tggactcgta cagagcgcca gcggctggca tcggttgtcg gcgccgtcgt gatcctgcat    2520
gtattgggcg tggccctgta tgtgggatac tccggtaatc cagcagccgc cggaggcctc    2580
gccggatccg gtgtgctcgc ctacgtgctc ggcgtccgcc acgcattcga cgccgatcac    2640
ctcgctgcca tcgatgacac cacgcgcctg atgctgttgc gcggacgccg tccggtcggg    2700
gtcgggttct tcttcgcgat gggacactcg accgtcgtca ttgtccttgc tctggtcgtg    2760
gcgctgggcg ccagctccct gaccacgagt gagctcgagg gggtccagga gatcggcgga    2820
atggtcgcga cggtcgtcgc cgtagccttc ttgctggtcg tcgccggact caacagcgtg    2880
gtcctgcgca atctgctctc cctggcccga cgggtgcgga ccggggcgga catcgcaggt    2940
gatctcgaga gcagcctcag cgagcgtggg ttgttcgccc ggctgctcgg tgcccgctgg    3000
cgtggactga ttcgttcgtc ctggcacatg tatccggtcg ggctgttgat ggggctcggg    3060
ctcgagaccg catccgaggt caccctgctc actctcactg cttcggcggt gaccgggggc    3120
accttgtccg tggctgcagc gggctcacgg acggatcggc cgccagatag tcgctcgcgg    3180
tgcgcgccag atgccagttc tgcag                                          3205
```

<210> SEQ ID NO 17
<211> LENGTH: 207
<212> TYPE: PRT
<213> ORGANISM: Rhodococcus rhodochrous

<400> SEQUENCE: 17

```
Met Thr Ala His Asn Pro Val Gln Gly Thr Leu Pro Arg Ser Asn Glu
 1               5                  10                  15

Glu Ile Ala Ala Arg Val Lys Ala Met Glu Ala Ile Leu Val Asp Lys
                20                  25                  30

Gly Leu Ile Ser Thr Asp Ala Ile Asp His Met Ser Ser Val Tyr Glu
            35                  40                  45

Asn Glu Val Gly Pro Gln Leu Gly Ala Lys Ile Val Ala Arg Ala Trp
        50                  55                  60

Val Asp Pro Glu Phe Lys Gln Arg Leu Leu Thr Asp Ala Thr Ser Ala
65                  70                  75                  80

Cys Arg Glu Met Gly Val Gly Gly Met Gln Gly Glu Glu Met Val Val
                85                  90                  95

Leu Glu Asn Thr Gly Thr Val His Asn Met Val Val Cys Thr Leu Cys
            100                 105                 110

Ser Cys Tyr Pro Trp Pro Val Leu Gly Leu Pro Pro Asn Trp Tyr Lys
        115                 120                 125
```

```
Tyr Pro Ala Tyr Arg Ala Arg Ala Val Arg Asp Pro Arg Gly Val Leu
        130                 135                 140

Ala Glu Phe Gly Tyr Thr Pro Asp Pro Asp Val Glu Ile Arg Ile Trp
145                 150                 155                 160

Asp Ser Ser Ala Glu Leu Arg Tyr Trp Val Leu Pro Gln Arg Pro Ala
                165                 170                 175

Gly Thr Glu Asn Phe Thr Glu Glu Gln Leu Ala Asp Leu Val Thr Arg
                180                 185                 190

Asp Ser Leu Ile Gly Val Ser Val Pro Thr Thr Pro Ser Lys Ala
        195                 200                 205

<210> SEQ ID NO 18
<211> LENGTH: 226
<212> TYPE: PRT
<213> ORGANISM: Rhodococcus rhodochrous

<400> SEQUENCE: 18

Met Asp Gly Ile His Asp Leu Gly Gly Arg Ala Gly Leu Gly Pro Ile
1               5                   10                  15

Lys Pro Glu Ser Asp Glu Pro Val Phe His Ser Asp Trp Glu Arg Ser
                20                  25                  30

Val Leu Thr Met Phe Pro Ala Met Ala Leu Ala Gly Ala Phe Asn Leu
            35                  40                  45

Asp Gln Phe Arg Gly Ala Met Glu Gln Ile Pro Pro His Asp Tyr Leu
        50                  55                  60

Thr Ser Gln Tyr Tyr Glu His Trp Met His Ala Met Ile His His Gly
65                  70                  75                  80

Ile Glu Ala Gly Ile Phe Asp Ser Asp Glu Leu Asp Arg Arg Thr Gln
                85                  90                  95

Tyr Tyr Met Asp His Pro Asp Asp Thr Thr Pro Thr Arg Gln Asp Pro
                100                 105                 110

Gln Leu Val Glu Thr Ile Ser Gln Leu Ile Thr His Gly Ala Asp Tyr
            115                 120                 125

Arg Arg Pro Thr Asp Thr Glu Ala Ala Phe Ala Val Gly Asp Lys Val
130                 135                 140

Ile Val Arg Ser Asp Ala Ser Pro Asn Thr His Thr Arg Arg Ala Gly
145                 150                 155                 160

Tyr Val Arg Gly Arg Val Gly Glu Val Val Ala Thr His Gly Ala Tyr
                165                 170                 175

Val Phe Pro Asp Thr Asn Ala Leu Gly Ala Gly Glu Ser Pro Glu His
                180                 185                 190

Leu Tyr Thr Val Arg Phe Ser Ala Thr Glu Leu Trp Gly Glu Pro Ala
            195                 200                 205

Ala Pro Asn Val Val Asn His Ile Asp Val Phe Glu Pro Tyr Leu Leu
        210                 215                 220

Pro Ala
225
```